US010058452B2

(12) United States Patent
Walter et al.

(10) Patent No.: US 10,058,452 B2
(45) Date of Patent: Aug. 28, 2018

(54) ONE-CARD PRESBYOPIA SYSTEMS AND RELATED METHODS

(71) Applicant: Wake Forest University Health Sciences, Winston-Salem, NC (US)

(72) Inventors: Keith Andrew Walter, Lewisville, NC (US); Evan Scott Luxon, Stanford, CA (US); Christopher Bligh Komanski, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 0 days.

(21) Appl. No.: 14/847,816

(22) Filed: Sep. 8, 2015

(65) Prior Publication Data

US 2015/0374547 A1 Dec. 31, 2015

Related U.S. Application Data

(62) Division of application No. 13/276,764, filed on Oct. 19, 2011, now Pat. No. 9,155,659.

(60) Provisional application No. 61/394,659, filed on Oct. 19, 2010.

(51) Int. Cl.
| | | |
|---|---|---|
| *A61B 18/20* | (2006.01) | |
| *A61F 9/008* | (2006.01) | |
| *A61B 34/00* | (2016.01) | |
| *A61B 34/10* | (2016.01) | |

(52) U.S. Cl.
CPC .......... *A61F 9/00802* (2013.01); *A61B 34/10* (2016.02); *A61B 34/25* (2016.02); *A61F 9/00808* (2013.01); *A61B 2034/108* (2016.02); *A61F 2009/00872* (2013.01); *A61F 2009/00878* (2013.01); *A61F 2009/00895* (2013.01)

(58) Field of Classification Search
CPC .............. A61F 9/00802; A61F 9/00804; A61F 9/00808; A61F 9/00814; A61F 2009/00861; A61F 2009/0087; A61F 2009/00872; A61F 2009/00885; A61F 2009/00895; A61B 34/10; A61B 34/25; A61B 2034/108
USPC .............................. 606/4–6, 10–12; 128/898
See application file for complete search history.

(56) References Cited

U.S. PATENT DOCUMENTS

| | | | |
|---|---|---|---|
| 5,533,997 | A | 7/1996 | Ruiz |
| 5,935,140 | A | 8/1999 | Buratto |
| 6,106,513 | A | 8/2000 | McMillen et al. |
| 6,139,542 | A | 10/2000 | Hohla |
| 6,149,643 | A | 11/2000 | Herekar et al. |

(Continued)

FOREIGN PATENT DOCUMENTS

| | | |
|---|---|---|
| WO | WO 1999/044492 | 9/1999 |
| WO | WO 2004/052253 | 6/2004 |
| WO | WO 2004/058113 A1 | 7/2004 |
| WO | WO 2006/012947 | 2/2006 |

OTHER PUBLICATIONS

Ang et al., Reversal of a presbyopic LASIK treatment, Clinical Ophthalmology, 2015, pp. 115-119, vol. 9.

(Continued)

*Primary Examiner* — Ahmed Farah
(74) *Attorney, Agent, or Firm* — Myers Bigel, P.A.

(57) ABSTRACT

Methods and systems for correcting presbyopia using a surgical excimer laser include activating the laser once and transmitting a pre-defined three dimensional ablation profile to treat presbyopia based on the single activating step.

8 Claims, 18 Drawing Sheets

(56) References Cited

U.S. PATENT DOCUMENTS

| | | | |
|---|---|---|---|
| 6,302,877 B1* | 10/2001 | Ruiz | A61F 9/00808 606/5 |
| 6,409,664 B1 | 6/2002 | Kattan et al. | |
| 6,814,729 B2 | 11/2004 | Youssefi et al. | |
| 6,843,787 B2 | 1/2005 | Ruiz | |
| 6,969,386 B2 | 11/2005 | Tamayo et al. | |
| 7,118,214 B2 | 10/2006 | Cox | |
| 7,220,255 B2 | 5/2007 | Lai | |
| 8,398,628 B2 | 3/2013 | Muller | |
| 8,409,181 B2 | 4/2013 | Bor | |
| 8,414,565 B2 | 4/2013 | Roberts et al. | |
| 8,486,055 B2 | 7/2013 | Knox et al. | |
| 8,556,886 B2 | 10/2013 | Youssefi | |
| 2003/0040738 A1 | 2/2003 | Ruiz et al. | |
| 2003/0069566 A1* | 4/2003 | Williams | A61F 9/00804 606/5 |
| 2004/0002695 A1 | 1/2004 | Youssefi et al. | |
| 2004/0059320 A1 | 3/2004 | Telandro et al. | |
| 2006/0195074 A1 | 8/2006 | Bartoli | |
| 2007/0203478 A1 | 8/2007 | Herekar | |
| 2007/0265603 A1 | 11/2007 | Pinelli | |
| 2009/0326650 A1 | 12/2009 | Zickler et al. | |
| 2012/0083776 A1* | 4/2012 | Dai | A61F 9/00804 606/5 |
| 2012/0296422 A1 | 11/2012 | Weeber | |

OTHER PUBLICATIONS

Bond et al., An Update on Presby-LASIK, Cataract & Refractive Surgery Today, Oct. 2009, pp. 21-22.

Epstein et al., Presbyopia Treatment by Monocular Peripheral PresbyLASIK, Journal of Refractive Surgery, Jun. 2009, pp. 516-523, vol. 25.

Heiting et al., PresbyLASIK (Multifocal LASIK, Bifocal LASIK or LASIK for Presbyopia), http://www.allaboutvision.com/visionsurgery/presby-lasik.htm, page updated May 2013, printed from the internet Dec. 2, 2013, 4 pages.

International Search Report and Written Opinion from corresponding PCT application No. PCT/US2011/056862, dated Jun. 27, 2012.

LASIK—Laser Vision Correction, http://www.lasikworld.com/20_questions_to_consider.html, 17 pages, printed from the internet Feb. 11, 2010.

Mosquera et al., Review: Presbyopic correction on the cornea, Eye and Vision, 2014, vol. 1, No. 5, 13 pages.

Papadopoulos et al., Current Management of Presbyopia, Middle East Afr J Ophthalmol., 2014, pp. 1-11, vol. 21, No. 1.

Pinelli et al., Correction of presbyopia in hyperopia with a center-distance, paracentral-near technique using the Technolas 217z platform, Journal of Refractive Surgery, 2008, pp. 494-500, vol. 24, No. 5.

Supplementary Partial European Search Report for related EP Application No. EP11835057, dated Dec. 23, 2014, 5 pages.

Wavefront Optimized® Ablation Profiles, http://www.alconsurgical.com/wavefront-optimized-ablation-profile.aspx, date unknown but believed to be before the priority date of the present application, printed from the internet Dec. 2, 2013, 4 pages.

Summons to Attend Oral Proceedings Pursuant to Rule 115(1) EPC corresponding to European Patent Application No. 11835057.8 (6 pages) (dated Sep. 20, 2017).

\* cited by examiner

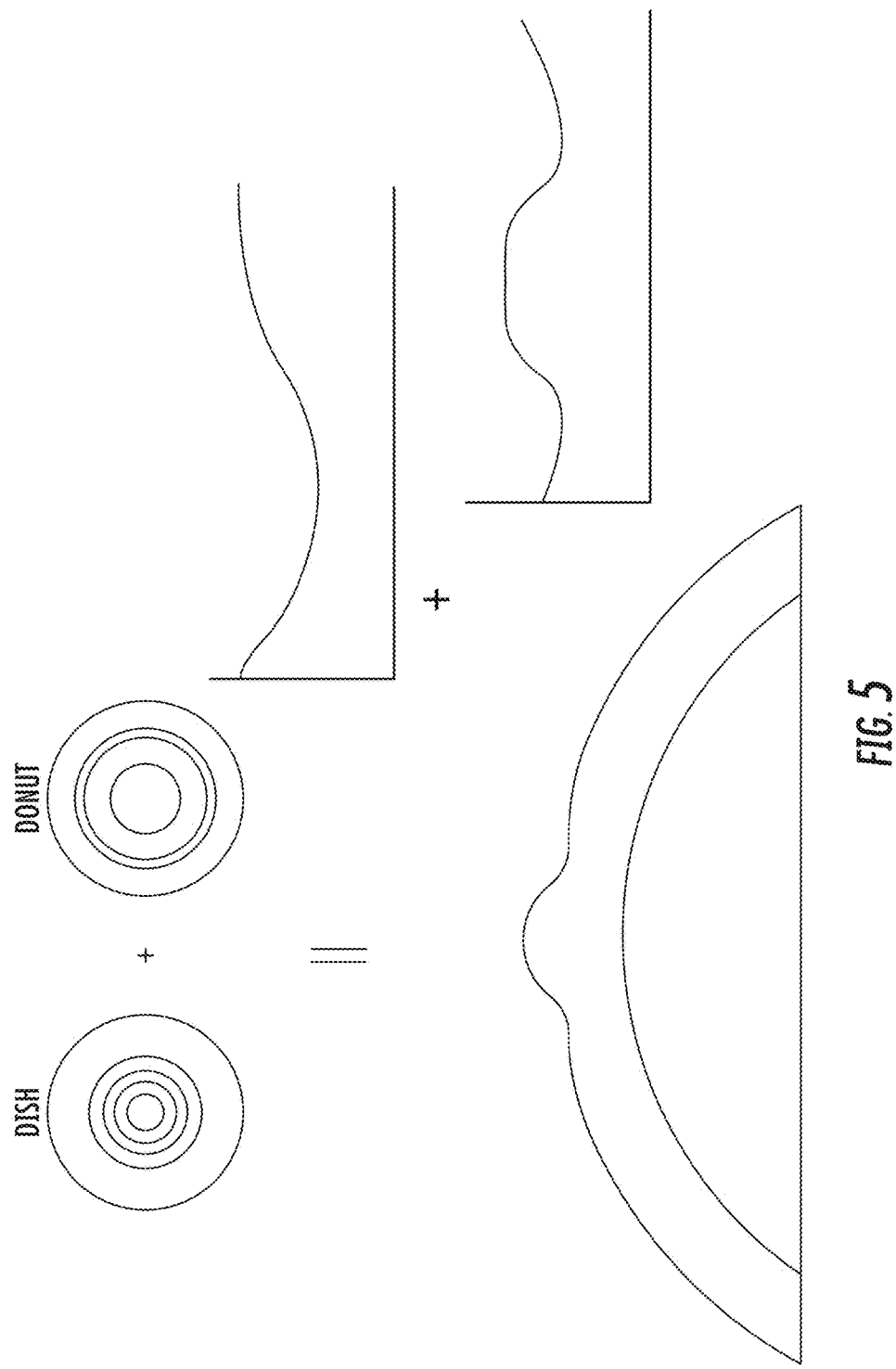

ABLATION PROFILES FOR r=-5

ABLATION PROFILES FOR r=-3
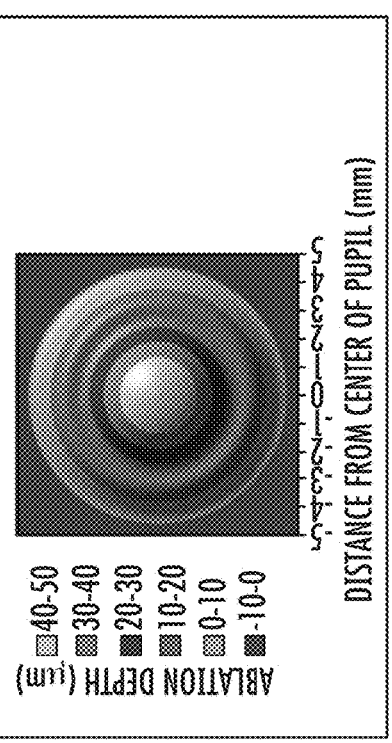
FIG. 7A
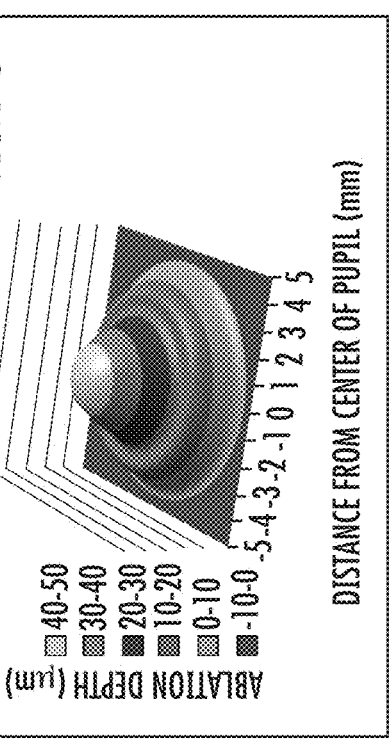
FIG. 7B
FIG. 7C

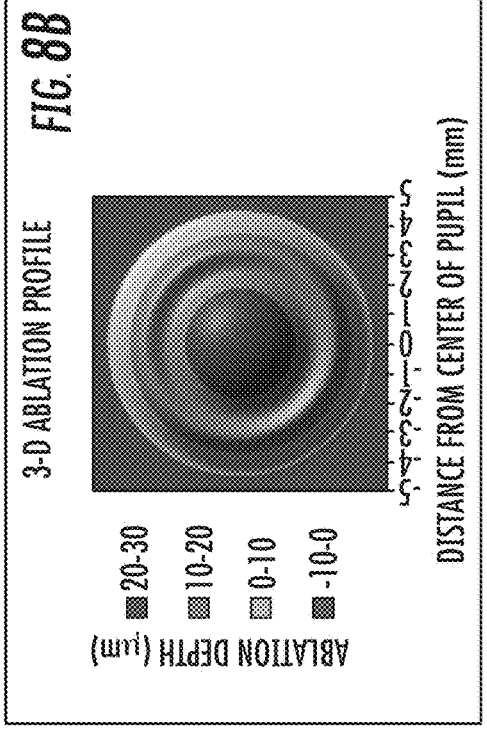
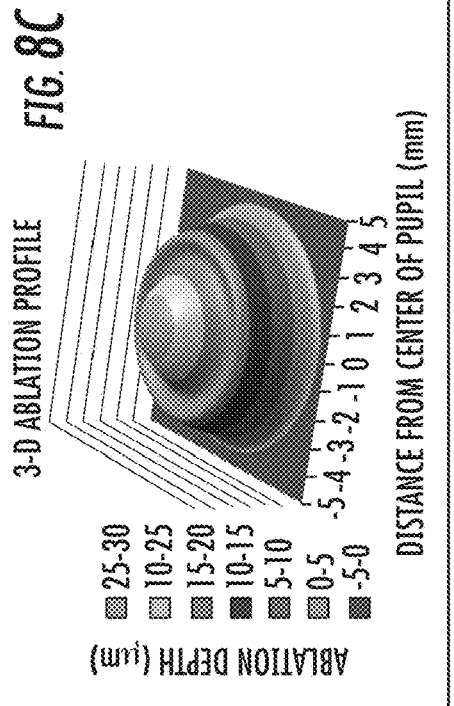
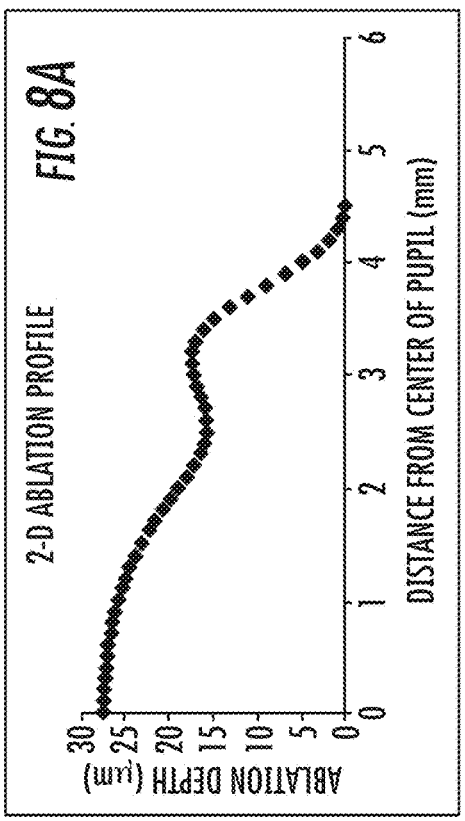

ABLATION PROFILES FOR r=0

ABLATION PROFILES FOR r=+1

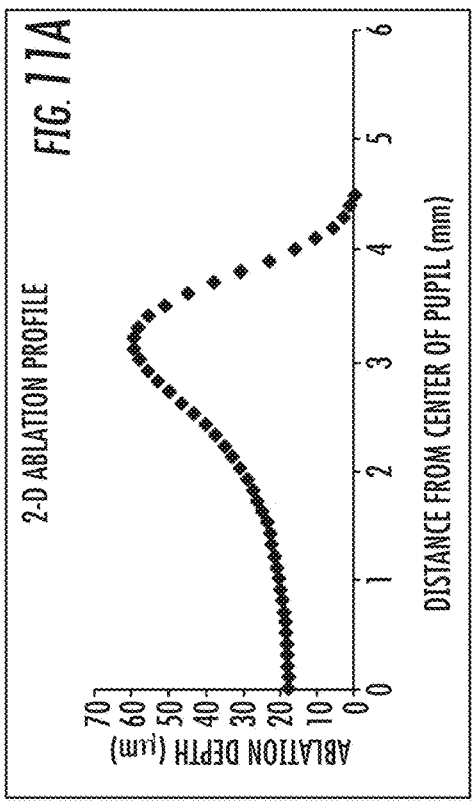
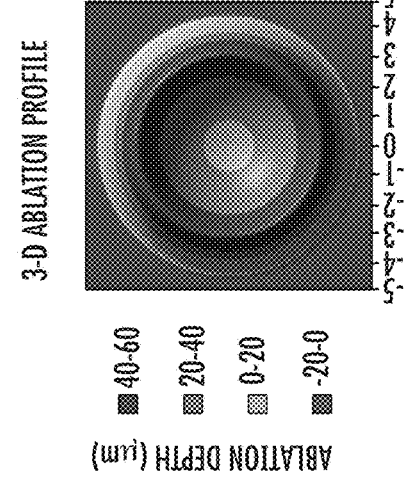
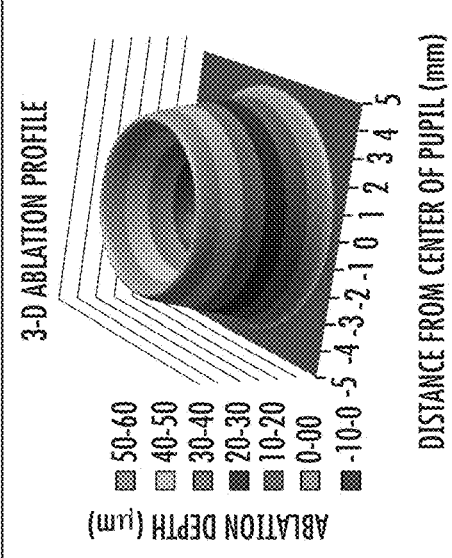
ABLATION PROFILES FOR r=+3
FIG. 11A
FIG. 11B
FIG. 11C ABLATION PROFILES FOR r=+5

| Parameters | | | Range | |
|---|---|---|---|---|
| Rx_m= | -1.5 | | -1.25 | -7.5 |
| Rx_h= | 1.25 | | 1.25 | 3.75 |
| z_m= | 5.5 | | 5 | 6.5 |
| z_h= | 6 | | 6 | 7 |

| | | Gumbel | | | | Lognormal | | |
|---|---|---|---|---|---|---|---|---|
| x | D_m | D_h | D_h | D | D_m | D_m | D_h | D_h | D |
| 0 | 17.54565 | 0.217225 | 0.217225 | 17.76287 | 16.91198 | 16.91198 | 0.407905 | 0.407905 | 17.31988 |
| 0.1 | 17.44552 | 0.282695 | 0.282695 | 17.72822 | 16.82009 | 16.82009 | 0.47281 | 0.47281 | 17.2929 |
| 0.2 | 17.32807 | 0.358553 | 0.358553 | 17.68662 | 16.71425 | 16.71425 | 0.547994 | 0.547994 | 17.26224 |
| 0.3 | 17.19046 | 0.446404 | 0.446404 | 17.63686 | 16.59224 | 16.59224 | 0.635036 | 0.635036 | 17.22728 |
| 0.4 | 17.02944 | 0.548084 | 0.548084 | 17.57752 | 16.4515 | 16.4515 | 0.735735 | 0.735735 | 17.18724 |
| 0.5 | 16.84132 | 0.665692 | 0.665692 | 17.50701 | 16.28907 | 16.28907 | 0.852139 | 0.852139 | 17.14121 |
| 0.6 | 16.62195 | 0.801617 | 0.801617 | 17.42357 | 16.10151 | 16.10151 | 0.986565 | 0.986565 | 17.08807 |
| 0.7 | 16.3667 | 0.958566 | 0.958566 | 17.32527 | 15.88489 | 15.88489 | 1.141627 | 1.141627 | 17.02652 |
| 0.8 | 16.07046 | 1.139599 | 1.139599 | 17.21006 | 15.63471 | 15.63471 | 1.320255 | 1.320255 | 16.95497 |
| 0.9 | 15.7277 | 1.348152 | 1.348152 | 17.07585 | 15.34584 | 15.34584 | 1.525716 | 1.525716 | 16.87155 |
| 1 | 15.33252 | 1.58806 | 1.58806 | 16.92058 | 15.01247 | 15.01247 | 1.761623 | 1.761623 | 16.77409 |
| 1.1 | 14.87883 | 1.863569 | 1.863569 | 16.7424 | 14.62813 | 14.62813 | 2.031937 | 2.031937 | 16.66007 |
| 1.2 | 14.36058 | 2.179333 | 2.179333 | 16.53991 | 14.18569 | 14.18569 | 2.340954 | 2.340954 | 16.52665 |
| 1.3 | 13.77205 | 2.540395 | 2.540395 | 16.31245 | 13.67742 | 13.67742 | 2.693269 | 2.693269 | 16.37069 |
| 1.4 | 13.10835 | 2.952129 | 2.952129 | 16.06048 | 13.09522 | 13.09522 | 3.093717 | 3.093717 | 16.18894 |
| 1.5 | 12.36601 | 3.420146 | 3.420146 | 15.78616 | 12.43089 | 12.43089 | 3.547272 | 3.547272 | 15.97817 |
| 1.6 | 11.54372 | 3.950139 | 3.950139 | 15.49386 | 11.67675 | 11.67675 | 4.058901 | 4.058901 | 15.73565 |
| 1.7 | 10.64322 | 4.547654 | 4.547654 | 15.19087 | 10.82638 | 10.82638 | 4.633355 | 4.633355 | 15.45974 |
| 1.8 | 9.67029 | 5.217764 | 5.217764 | 14.88805 | 9.875974 | 9.875974 | 5.274886 | 5.274886 | 15.15086 |
| 1.9 | 8.63572 | 5.964615 | 5.964615 | 14.60033 | 8.82603 | 8.82603 | 5.986874 | 5.986874 | 14.8129 |
| 2 | 7.556075 | 6.790826 | 6.790826 | 14.3469 | 7.683787 | 7.683787 | 6.771346 | 6.771346 | 14.45513 |

*FIG. 14A-1*

| | | | | | | | | | |
|---|---|---|---|---|---|---|---|---|---|
| 2.1 | 6.454086 | 7.696714 | 7.696714 | 14.1508 | 6.466251 | 6.466251 | 7.628367 | 7.628367 | 14.09462 |
| 2.2 | 5.358311 | 8.679323 | 8.679323 | 14.03763 | 5.203676 | 5.203676 | 8.555307 | 8.555307 | 13.75898 |
| 2.3 | 4.301794 | 9.731254 | 9.731254 | 14.03305 | 3.942805 | 3.942805 | 9.545968 | 9.545968 | 13.48877 |
| 2.4 | 3.319497 | 10.83931 | 10.83931 | 14.15881 | 2.748318 | 2.748318 | 10.58958 | 10.58958 | 13.3379 |
| 2.5 | 2.444525 | 11.98305 | 11.98305 | 14.42757 | 1.699496 | 1.699496 | 11.66974 | 11.66974 | 13.36924 |
| 2.6 | 1.703552 | 13.13328 | 13.13328 | 14.83683 | 0.877519 | 0.877519 | 12.76327 | 12.76327 | 13.64079 |
| 2.7 | 1.112332 | 14.2509 | 14.2509 | 15.36323 | 0.338895 | 0.338895 | 13.83922 | 13.83922 | 14.17811 |
| 2.8 | 0.672561 | 15.28612 | 15.28612 | 15.95868 | 0.078025 | 0.078025 | 14.85812 | 14.85812 | 14.93615 |
| 2.9 | 0.371387 | 16.17885 | 16.17885 | 16.55024 | 0.006038 | 0.006038 | 15.77175 | 15.77175 | 15.77779 |
| 3 | 0.184254 | 16.86044 | 16.86044 | 17.04469 | 1.78E-05 | 1.78E-05 | 16.52371 | 16.52371 | 16.52372 |
| 3.1 | 0.080559 | 17.25769 | 17.25769 | 17.33824 | #NUM! | 0 | 17.05123 | 17.05123 | 17.05123 |
| 3.2 | 0.03034 | 17.29934 | 17.29934 | 17.32968 | #NUM! | 0 | 17.28871 | 17.28871 | 17.28871 |
| 3.3 | 0.009582 | 16.92544 | 16.92544 | 16.93502 | #NUM! | 0 | 17.17326 | 17.17326 | 17.17326 |
| 3.4 | 0.002458 | 16.09888 | 16.09888 | 16.10134 | #NUM! | 0 | 16.65254 | 16.65254 | 16.65254 |
| 3.5 | 0.000493 | 14.81785 | 14.81785 | 14.81834 | #NUM! | 0 | 15.69482 | 15.69482 | 15.69482 |
| 3.6 | 7.41E-05 | 13.12639 | 13.12639 | 13.12647 | #NUM! | 0 | 14.30031 | 14.30031 | 14.30031 |
| 3.7 | 7.92E-06 | 11.11946 | 11.11946 | 11.11947 | #NUM! | 0 | 12.51204 | 12.51204 | 12.51204 |
| 3.8 | 5.65E-07 | 8.938507 | 8.938507 | 8.938508 | #NUM! | 0 | 10.42332 | 10.42332 | 10.42332 |
| 3.9 | 2.5E-08 | 6.755049 | 6.755049 | 6.75505 | #NUM! | 0 | 8.177504 | 8.177504 | 8.177504 |
| 4 | 6.32E-10 | 4.742884 | 4.742884 | 4.742884 | #NUM! | 0 | 5.955801 | 5.955801 | 5.955801 |
| 4.1 | 8.22E-12 | 3.044675 | 3.044675 | 3.044675 | #NUM! | 0 | 3.950336 | 3.950336 | 3.950336 |
| 4.2 | 4.89E-14 | 1.742977 | 1.742977 | 1.742977 | #NUM! | 0 | 2.324293 | 2.324293 | 2.324293 |
| 4.3 | 1.15E-16 | 0.846861 | 0.846861 | 0.846861 | #NUM! | 0 | 1.168996 | 1.168996 | 1.168996 |
| 4.4 | 9.14E-20 | 0.30049 | 0.30049 | 0.30049 | #NUM! | 0 | 0.476057 | 0.476057 | 0.476057 |
| 4.5 | 2E-23 | 0.010379 | 0.010379 | 0.010379 | #NUM! | 0 | 0.144482 | 0.144482 | 0.144482 |
| 4.6 | 9.57E-28 | -0.12112 | 0 | 9.57E-28 | #NUM! | 0 | 0.028567 | 0.028567 | 0.028567 |
| 4.7 | 7.62E-33 | -0.17082 | 0 | 7.62E-233 | #NUM! | 0 | 0.002906 | 0.002906 | 0.002906 |
| 4.8 | 7.3E-39 | -0.18606 | 0 | 7.3E-39 | #NUM! | 0 | 9.57E-05 | 9.57E-05 | 9.57E-05 |
| 4.9 | 5.75E-46 | -0.18973 | 0 | 5.75E-46 | #NUM! | 0 | 3.44E-07 | 3.44E-07 | 3.44E-07 |

FIG. 14A-2

| | | | | | | | |
|---|---|---|---|---|---|---|---|
| | | | | | 0 | 3.96E-12 | 3.96E-12 |
| | | | | | 0 | 3.96E-12 | 3.96E-12 |
| | | | | | 0 | 7.63E-34 | 7.63E-34 |
| | | | | | 0 | 7.63E-34 | 0 |
| 5 | 2.37E-54 | -0.1904 | 0 | 2.37E-54 | 0 | #NUM! | 0 |
| 5.1 | 3.01E-64 | -0.19049 | 0 | 3.01E-64 | 0 | #NUM! | 0 |
| 5.2 | 6.27E-76 | -0.1905 | 0 | 6.27E-76 | 0 | #NUM! | 0 |
| 5.3 | 1.02E-89 | -0.1905 | 0 | 1.02E-89 | 0 | #NUM! | 0 |
| 5.4 | 5.4E-106 | -0.1905 | 0 | 5.4E-106 | 0 | #NUM! | 0 |
| 5.5 | 3.4E-125 | -0.1905 | 0 | 3.4E-125 | 0 | #NUM! | 0 |
| 5.6 | 7.1E-148 | -0.1905 | 0 | 7.1E-148 | 0 | #NUM! | 0 |
| 5.7 | 1.2E-174 | -0.1905 | 0 | 1.2E-174 | 0 | #NUM! | 0 |
| 5.8 | 3.2E-206 | -0.1905 | 0 | 3.2E-206 | 0 | #NUM! | 0 |
| 5.9 | 1.7E-243 | -0.1905 | 0 | 1.7E-243 | 0 | #NUM! | 0 |
| 6 | 1.7E-287 | -0.1905 | 0 | 1.7E-287 | 0 | #NUM! | 0 |

FIG. 14A-3

ONE-CARD PRESBYOPIA SYSTEMS AND RELATED METHODS

RELATED APPLICATIONS

This patent application is a divisional application of U.S. patent application Ser. No. 13/276,764, filed Oct. 19, 2011, which claims the benefit of and priority to U.S. Provisional Application Ser. No. 61/394,659 filed Oct. 19, 2010, the contents of which are hereby incorporated by reference as if recited in full herein.

FIELD OF THE INVENTION

This invention relates to laser systems for vision correction.

BACKGROUND OF THE INVENTION

Over the past several years, a technique termed "presby-LASIK" has been used to treat patients with presbyopia with promising results. "LASIK" is an acronym for Laser-Assisted In situ Keratomileusis excimer laser vision correction surgery. The so-called "double card" treatment adds negative aspericity by altering the mid-periphery of the cornea (also known as increased prolate shape). See, e.g., *An Update on Presby-LASIK*, Bond et al., Cataract & Refractive Surgery Today, October 2009, pp. 21-22. See also, U.S. Patent Application Serial No. 2007/0265603 to Pinelli and U.S. Pat. No. 6,139,542, the contents of which are hereby incorporated by reference as if recited in full herein.

Unfortunately, the double-card procedure involves the use of two encrypted key cards that control the operation of the excimer laser with two associated, separate activations of the laser for each eye. The downtime of the laser between firings can be between about 30 seconds to about 1 minute (or longer) which can affect the outcome of the procedure, as the laser can have a different calibration upon re-activation of the laser, the laser can be misaligned with the first ablation treatment and/or the eye, the pupil size may vary, and/or the like.

SUMMARY OF EMBODIMENTS OF THE INVENTION

Embodiments of the invention are directed to providing systems that can be used to treat presbyopia in a patient.

The systems can direct a laser to ablate the cornea with a defined three-dimensional presby ablation profile for presbyobic correction of a patient using a single activation of the laser.

The ablation profile can create a prolate-shaped cornea with negative aspericity resulting in a multi-focal cornea and/or increasing depth of field without reducing distance acuity. The prolate shape can be more pronounced relative to conventional LASIK or PRK ablations.

The patient may be neither hyperopic nor myopic, but a so-called emmetropic presbyope. Other situations for presbyopic corrections may include correcting the patient's distance requirement as well, whether that is, myopia, hyperopia, or astigmatism. The systems can be used to treat plano presbyopes as well.

The system can be a "one-card" system. The system may be a universal one-card that can be used to treat presbyopia in most (if not all) suitable emmetropic presbyope candidate patients. The one-card laser control system can improve reading vision (e.g., to obviate the need for +2 or less (e.g., about +1.5 to about +2) readers without requiring pre-surgery calibration measurements of the patient's cornea contour or anatomical features.

Some aspects of the invention are directed to methods of correcting presbyopia, including activating a surgical excimer laser once; and ablating a patient's eye using a defined three dimensional presby ablation profile to treat presbyopia based on the activating step.

The ablating step can be carried out using at least one controller that is in communication with the laser. The at least one controller can be configured to generate the three dimensional presby ablation profile using a defined mathematical equation and the equation can include a parameter for myopic correction and a parameter for hyperopic correction.

The three dimensional presby ablation profile can be generated using a defined mathematical equation derived from a distribution of ablation data from separate myopic and hyperopic ablation profiles and the equation includes an input parameter for myopic correction and an input parameter for hyperopic correction.

Some embodiments are directed to presbyopia treatment systems. The systems include: (a) an excimer laser configured to ablate a cornea with a defined three-dimensional presby ablation profile that is generated using a single activation of the laser to treat presbyopia; and (b) a controller in communication with the laser configured to direct the laser to generate the defined ablation profile.

The controller can be configured to generate the three dimensional presby ablation profile using a defined mathematical equation, and wherein the equation includes a parameter for myopic correction and a parameter for hyperopic correction.

The equation may also include at least one optical zone parameter.

The equation can include first and second optical zone parameters, one for a myopic optical zone and one for a hyperopic optical zone.

The mathematical equation can be derived from a Gumbel-distribution of empirical ablation data from separate myopic and hyperopic ablation profiles.

The mathematical equation can be derived from a log-normal-distribution of empirical ablation data from separate myopic and hyperopic ablation profiles.

The ablation profile creates a prolate shaped cornea with negative aspericity resulting in a multi-focal cornea and/or increasing depth of field without reducing distance acuity.

The defined presby ablation profile is for emmetrope presbyopia.

The defined laser presbyopia ablation profile is a universal ablation profile suitable for treating most emmetrope presbyopic patients without requiring in situ patient-specific adjustments.

The method can include inserting an encrypted data card into a reader associated with the laser to electronically authorize the laser to power up a single time to carry out the ablating step.

The method can include electronically requesting an authorization code for performing a presbyopia treatment from a remote site; then receiving an authorization code that is accepted by the laser that electronically activates the laser and electronically selects the presby three-dimensional profile for the presbyopia treatment.

The laser can be in communication with a remote site. The method can further include electronically requesting the activating of the laser for performing the presbyopia treatment from the remote site; wherein, upon confirmation of an approved treatment site and payment, the remote site electronically activates the laser and/or allows the ablating step.

The laser can be in communication with a computer interface that allows a remote site to control activation of the laser via the Internet, and the computer interface can control the number of activations based on a number of laser-specific or site-specific pre-paid activations.

The laser can be in communication with a computer internet interface that allows a remote site to control activation of the laser, and wherein the computer interface controls a number of times the activating step is allowed based on a number of pre-paid presby-specific activations associated with the laser and/or treatment site.

The activating step can have a higher per activation cost relative to presbyopic correction using the same laser with two-activations to treat presbyopia.

Other embodiments are directed to presbyopia treatment systems that include an excimer laser configured to ablate a cornea with a defined three-dimensional presby ablation profile that is generated using a single activation of the laser to treat presbyopia and a controller in communication with the laser configured to direct the laser to generate the defined ablation profile.

The controller can be configured to generate the three dimensional presby ablation profile using a defined mathematical equation derived from a distribution of defined ablation data from separate myopic and hyperopic ablation profiles, and the equation includes a parameter for myopic correction and a parameter for hyperopic correction.

The excimer laser can be in communication with a computer interface that allows a remote site, via the Internet, to (a) control activation of the laser and (b) inactivate the laser based on defined contract rules.

The system can include an electronic reader in communication with the laser and controller. The controller can be configured to activate the laser based on an activation card read by the reader.

The system can be configured so that the defined presbyopia ablation profile is a universal ablation profile suitable for treating most emmetropic presbyope patients without requiring in situ patient-specific adjustments.

The system ablation profile can be used to treat an ametropic presbyope patient.

The controller can include a computer interface that communicates with a remote site to obtain an authorization code used to activate the laser, allow a presby mode and/or inactivate the laser.

The system can include a user interface that allows a user to enter an authorization code that directs the laser to activate and selects the defined presbyopic ablation profile.

The system controller can be in communication with a user interface and a user at the laser site can electronically select a presbyopic treatment from a menu of different vision correction procedures and the controller can direct the laser to transmit the defined presbyopic ablation profile when a presby-specific laser activation authorization code is entered.

The controller can be in communication with a global computer network and the controller is configured to electronically request a presby-specific authorization code from a remote site to activate the laser.

The controller can be in communication with a global computer network that allows the controller to electronically request activation of the laser for performing a presbyopia treatment from the remote site or electronically request an authorization code for activating the laser.

The laser can be in communication with a computer interface that allows the remote site to control activation of the laser via the Internet, and the computer interface controls the number of activations of the laser based on a number of laser-specific and/or site-specific pre-paid activations.

The controller can be in communication with a computer interface that allows the remote site to control activation of the laser via the Internet, and the computer interface controls the number of activations of the laser for transmitting the defined presbyopic ablation profile based on a number of pre-paid presby-specific activations.

The laser can be in communication with a computer interface that allows a remote site, via the Internet, to (a) control activation of the laser and (b) inactivate the laser based on defined contract rules.

The ablation profile can create a prolate shaped cornea with negative asphericity resulting in a multi-focal cornea and/or increasing depth of field without reducing distance acuity.

The defined presbyopia ablation profile can be a universal ablation profile suitable for treating most emmetropic presbyope patients without requiring in situ patient-specific adjustments.

The systems may be configured to provide corrections for piano, myopia, emmetropia or hyperopia presbyope and/or astigmatism.

The same equation can be used for different patients, the equation having adjustable myopic and hyperopic input parameters that can be selected according to a patient's vision and desired treatment.

Yet other embodiments are directed to a computer program product for operating a laser system. The computer program product includes a non-transitory computer readable storage medium having computer readable program code embodied in the medium. The computer-readable program code includes computer readable program code configured to direct a therapeutic excimer laser to transmit a pre-defined presbyopia three dimensional ablation profile to treat presbyopia based on a single activation of the excimer laser and computer readable program code that defines a mathematical equation for the ablation profile with multiple parameters, including an adjustable parameter for myopic correction and an adjustable parameter for hyperopic correction.

The ablation profile can optionally create a prolate shaped cornea with negative asphericity resulting in a multi-focal cornea and/or increasing depth of field without reducing distance acuity.

The foregoing and other objects and aspects of the present invention are explained in detail in the specification set forth below.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

BRIEF DESCRIPTION OF THE DRAWINGS

FIG. 5 is a schematic illustration of a 3-D presby ablation profile that has combined corrections (generates a single ablation profile where a conventional treatment used two separate ablations) according to embodiments of the present invention.

FIGS. 6A, 7A, 8A, 9A, 10A, 11A and 12A illustrate 2-D ablation profiles of ablation depth (vim) versus distance from the center of the cornea or pupil (mm). The other corresponding figures, FIGS. 6B, 6C, 7B, 7C, 8B, 8C, 9B, 9C, 10B, 10C, 11B, 11C and 12B, 12C show the 2-D ablation pattern in 3-D, by revolving the respective 2-D curve around a line at the center of the cornea.

FIG. 14A is a table or spread sheet (provided as FIGS. 14A1-3) of adjustable parameters for calculating a presby ablation profile according to some embodiments of the present invention.

DESCRIPTION OF EMBODIMENTS OF THE INVENTION

Figure 1:
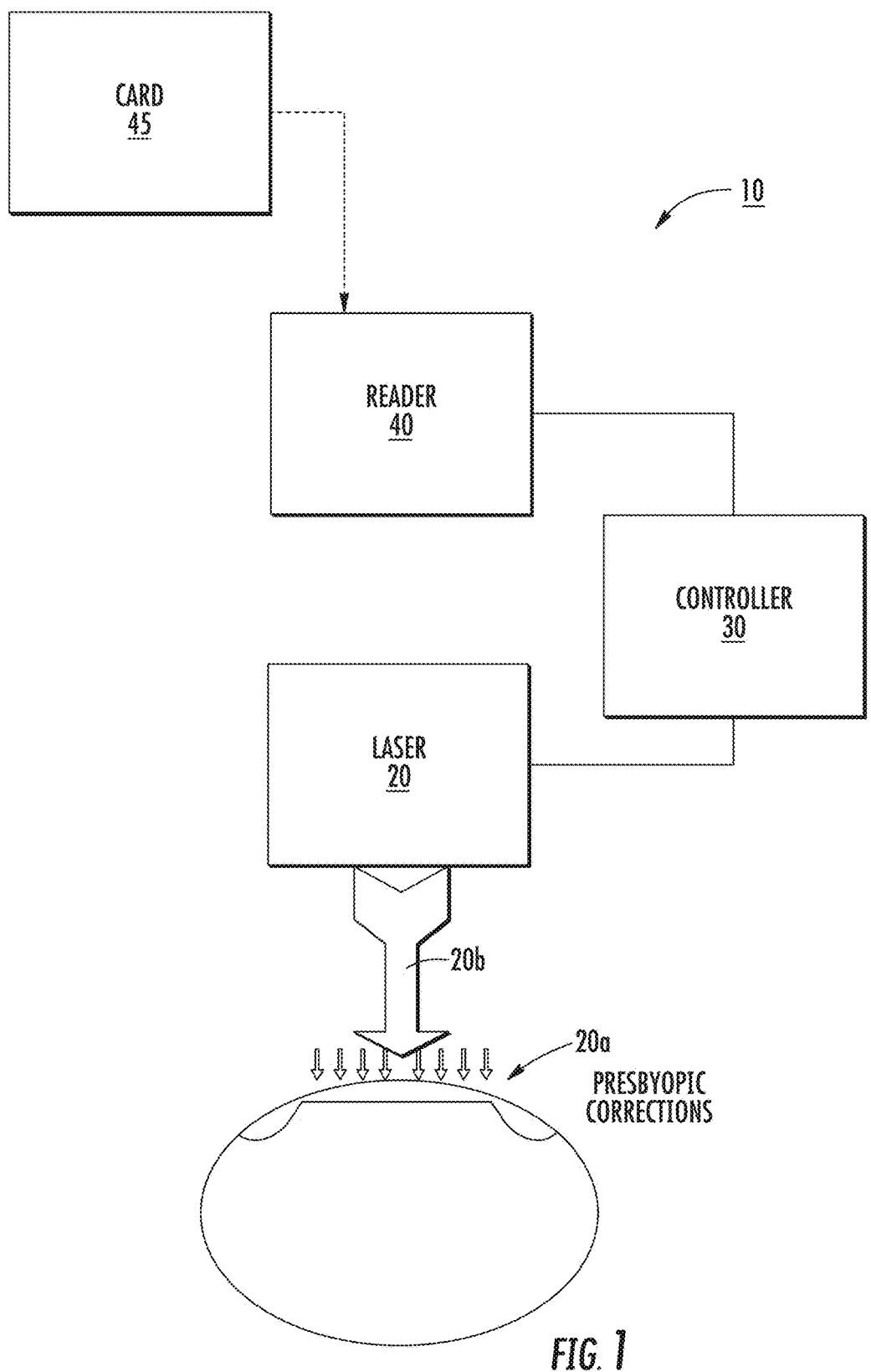
FIG. 1 is a schematic illustration of an excimer laser system used to treat presbyopia according to embodiments of the present invention.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the figures and/or claims unless specifically indicated otherwise. In the drawings, the thickness of lines, layers, features, components and/or regions may be exaggerated for clarity and broken lines illustrate optional features or operations, unless specified otherwise.

The terminology used herein is for the purpose of describing particular embodiments only and is not intended to be limiting of the invention. As used herein, the singular forms, "a", "an" and "the" are intended to include the plural forms as well, unless the context clearly indicates otherwise. It will be further understood that the terms "comprises," "comprising," "includes," and/or "including" when used in this specification, specify the presence of stated features, regions, steps, operations, elements, and/or components, but do not preclude the presence or addition of one or more other features, regions, steps, operations, elements, components, and/or groups thereof.

It will be understood that when a feature, such as a layer, region or substrate, is referred to as being "on" another feature or element, it can be directly on the other feature or element or intervening features and/or elements may also be present. In contrast, when an element is referred to as being "directly on" another feature or element, there are no intervening elements present. It will also be understood that, when a feature or element is referred to as being "connected", "attached" or "coupled" to another feature or element, it can be directly connected, attached or coupled to the other element or intervening elements may be present. In contrast, when a feature or element is referred to as being "directly connected", "directly attached" or "directly coupled" to another element, there are no intervening elements present. Although described or shown with respect to one embodiment, the features so described or shown can apply to other embodiments.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein.

The term "card" refers to any device that has electronic memory or optically or other electronically readable indicia that includes defined authorization codes or data (typically encrypted) that can be used to activate the excimer laser 20. Thus, the term "card" includes all types of portable media including, but not limited to, plastic cards, USB memory sticks, and digital memory cards (e.g., removable flash memory card format).

The term "controller" refers to at least one processor that includes computer program code or a circuit that generates a defined ablation profile. The controller and/or at least one processor can be on-board a local laser system or partly or totally held at a remote site to communicate with the local laser via a global computer network such as the Internet or a local area network (LAN).

The term "optical zone" refers to an input parameter based on a width of the patients' cornea or portions thereof. With respect to the word "scale" used for the optical zone parameter, this term refers to a value derived from empirical data from existing ablation patterns, which can be fit using a linear model. So, for any given constant in a conventional/original ablation profile, that same constant can be scaled linearly for a variety of corneal widths in order to obtain a desired or correct profile (e.g., in the equations in the example section, this takes the form (a*z+b)).

The terms "distribution function" and "distribution" are used interchangeably herein to refer to a statistical function or model, typically an asymmetric continuous distribution, used to fit empirical data associated with separate or distinct ablation patterns for myopic and hyperopic corrections (ablation depth versus distance from a center of a pupil or cornea) to combine those separate ablation profiles into a single, composite or summed ablation profile for presby vision correction. Thus, the distribution, where used, fits the ablation profile data from two separate known ablation profiles (one for myopic and one for hyperopic correction) and combines these separate ablation profiles to form a composite or cumulative single ablation profile for Presby-LASIK or PresbyPRK. The empirical profile data can be created by entering patient parameters (correction and optical zone) into a standard commercially available system, e.g., a LASIK or PRK system, and generating the corresponding profile data (ablation depth and distance from the center of the pupil).

While the lognormal and Gumbel distribution functions are particularly described herein, other distributions can be used to fit the empirical data for mathematical models or equations to define an appropriate presby ablation profile, including Beta distribution, Birnbaum-Saunders distribution, Chi-squared distribution, F-distribution, Fréchet distribution, Gamma distribution, Landau distribution, Lévy distribution, Power-lognormal distribution, Rayleigh distribution, Skew normal distribution and Weibull distribution including combinations of any of the above.

The patient may be emmetropic presbyope or ametropic presbyope. As noted above, the emmetopric presbyope is neither hyperopic nor myopic. These people are normal sighted for distance and typically only need reading glasses after about age 40 (although this condition may onset earlier for some people). In the case of emmetrope, the ablation profiles are typically well-defined and consistent across different patients. For example, in these patients, the double card is typically about −1.50 myopic ablation followed by about a +1.50 hyperopic ablation, or other serial or sequential −/+ patterns, such as −1.75/+2.00, −2.00/+2.25, and the like. There may be a small −/+ variance, such as, for example, −1.25/+1.50, or −1.50/+1.25 that some surgeons prefer. In the case of ametrope, the ablations can incorporate distance correction as well. That is, other situations for presbyopic corrections may include, for example, correcting the patients distance requirement as well, whether that be myopia, hyperopia, or astigmatism.

Referring now to the figures, FIG. 1 illustrates a vision correction system 10, such as a PRK or LASIK system 10, with an excimer laser 20, controller 30 and reader 40. Similar to conventional PRK or LASIK systems 10, the reader 40 can be configured to electronically or optically read an encrypted card 45 that controls activation of the laser 20. The reader 40 can decrement the number of activations remaining on the card (based on electronic memory held by the card 45 or based on electronic memory associated with the controller 30, reader 40 or other component of the excimer laser system 10).

Typically, each card 45 has a defined number of pre-paid excimer laser activations (such as 50), with a per-activation charge of about $200 (e.g., about $175 or about $150 at the time of the filing of this patent application). Once depleted, a new card is used to activate the excimer laser. During conventional refractive LASIK surgery, for example, the card 45 will be used to activate the excimer laser twice, once for each eye. For a "double-card" prebyopia treatment, the card 45 will be used to activate the excimer laser twice for each eye: once to ablate for hyperopic correction, and once to ablate for myopic correction. The excimer laser 20 is typically powered down between the two ablation treatments.

Referring again to FIG. 1, the system 10 can be configured to direct the excimer laser 20 to transmit a beam 20b that generates a defined three-dimensional ablation profile 20a for presbyopic correction (either emmetrope or ametrope presbyope corrections) using a single activation of the excimer laser 20. No special mask or other device is required. Embodiments of the present invention may be particularly suitable for single-card emmetropic presbyope correction of each eye. The lighting can be controlled to control pupil size.

Examples of commercial LASIK systems include the LADARVision® CustomCornea® system, VISX® Custom-Vue™ and WavePrint™ system, Bausch & Lamb's Technolas® Zyoptix™ system, and the Allegretto™ laser eye surgery system. All of these systems are stated to be able to provide custom, precise, personalized treatment, a smooth reshaping of the cornea, and decreased risk of undesirable side effects. Embodiments of the invention can alternatively or additionally be used with PRK (photorefractive keratectomy) systems which was once the most common refractive surgery procedure before LASIK and may still be preferred for certain patients or treatments. Thus, the system 10 can include either or both a PresbyPRK and a PresbyLASIK system.

According to embodiments of the present invention, the excimer laser systems 10 can be configured to treat emmetropic presbyopia using a "universal" ablation profile 20a that does not require patient-specific customization of adjustment in order to achieve an improvement in reading vision. The word "universal" means that the ablation profile can be used for many different presbyopia patients without requiring any further customization without compromising distance acuity. The ablation can result in a more prolate shaped cornea (over conventional two-card presby ablation treatments) that produces a multifocal effect and/or increase in a depth of field (e.g., typically about +2 or less, although +2.5 or more may be feasible as well) without compromising distance acuity.

Although shown in FIG. 1 as a single controller 30, more than one controller may be used. Also, the controller 30 can be located on-board the excimer laser 20 or can be a remote controller (whether in the same cabinet, in the room or even off-site from the excimer laser). The controller 30 can include software and hardware aspects. Accordingly, features of the present invention may take the form of an entirely software embodiment or an embodiment combining software and hardware aspects all generally referred to herein as a "circuit" or "module."

Figure 2A:
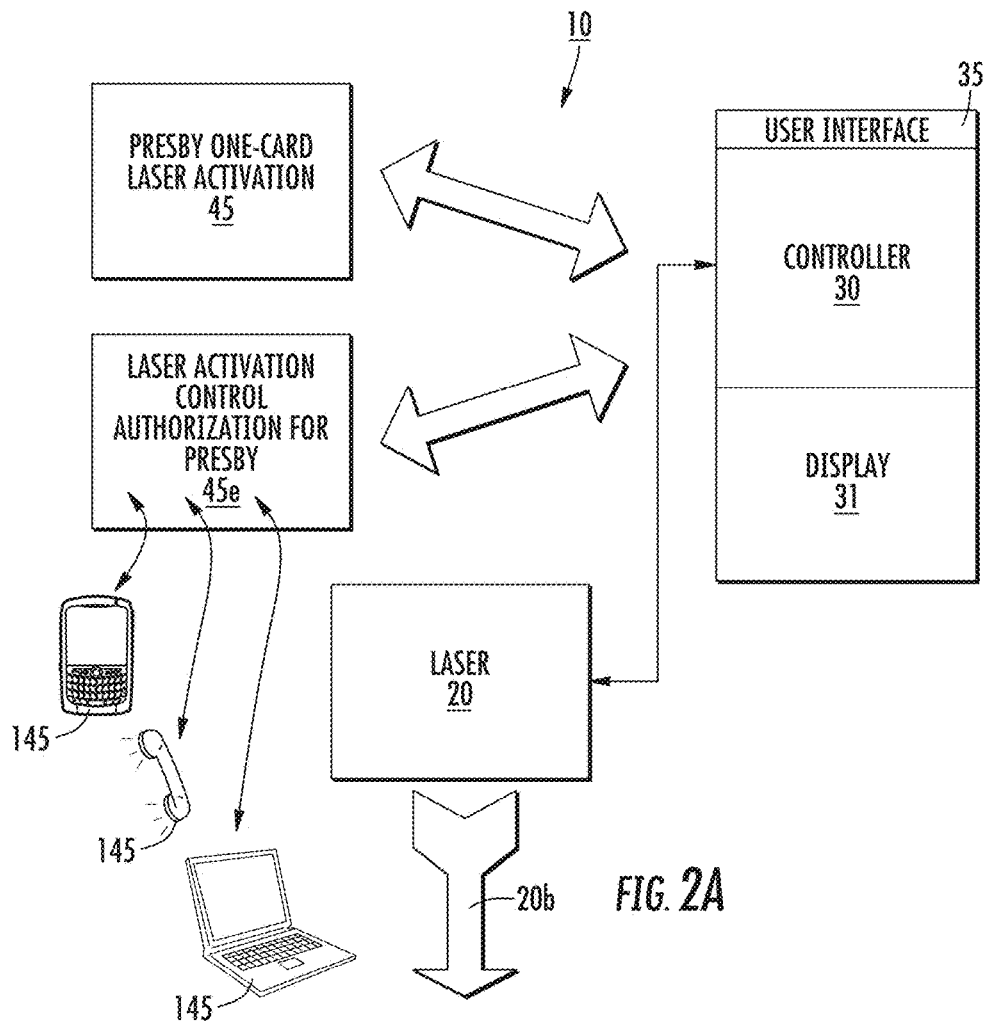
FIG. 2A is a schematic illustration of another excimer laser system used to treat presbyopia according to embodiments of the present invention.

FIG. 2A illustrates that the controller 30 can be in communication with a display 31 and a User Interface (UI) 35 that allows a user to communicate with the system 10. As before, an authorization code can be used to allow a one-activation presby mode and/or activate (or inactivate) the excimer laser 20. The code can be obtained from a card 45 or from an electronic device 45e and the authorization code can be manually or wirelessly entered using the UI 35 and the device 45e.

As shown, if a card 45 is used, the card 45 can be a presby-specific activation card 45 that allows the controller 30 and/or excimer laser 20 to generate the presby-ablation profile 20a. This card 45 may be priced above other single-card procedures but under the "double-card" presbyopia procedure, e.g., a 20% discount over two activations. For example, if a single activation is $150, then the presby-one-activation procedure can be priced at between $200-250 (below the $300 for a double card procedure). In another example, if a single activation is $175, the double card would be $350, then the presby-one card activation procedure can be priced at between about $200-300 (below the $350 dual card procedure, e.g., at 50%-90%, such as about 60-90%, or about 70-80%).

When an electronic authorization code 45e is used (apart from the card 45), the authorization code can be sent to the local site (or a user associated with the local laser site) such as a cellular telephone of record or an email address associated with a site-computer or mobile communication device, including a PDA, IPhone, IPOD, IPAD, PALM, electronic NOTEBOOK, smart phone, laptop or other pervasive computing device. The authorization code can be sent as a text message (optionally using SMS), email or the like (even as a voice message to a telephone).

In other embodiments, the card 45 can be reloadable with additional authorization codes using a local electronic download device that allows a user to pay for additional activations and communicates with a remote site 200 (FIG. 2B) to receive additional authorizations.

Figure 2C:
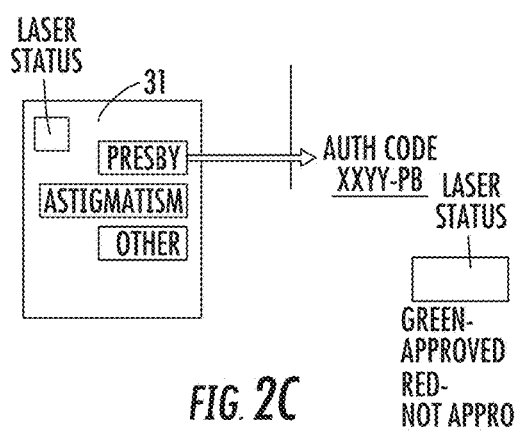
FIG. 2C is another schematic illustration of an excimer laser system.

The UI 35 can be a touch screen, mouse-based, keypad, voice-based input or other suitable input means. The UI 35 can be configured to allow a user to select the presbyopia treatment using a pull-down menu or other prompt as shown, for example in FIG. 2C. When selected, the UI asks for the authorization code (which can be presby-specific). If the code is approved, the UI can show a "green" approved status feedback on the display 31. Other user visual and/or audio visual indications can be used.

Figure 2B:
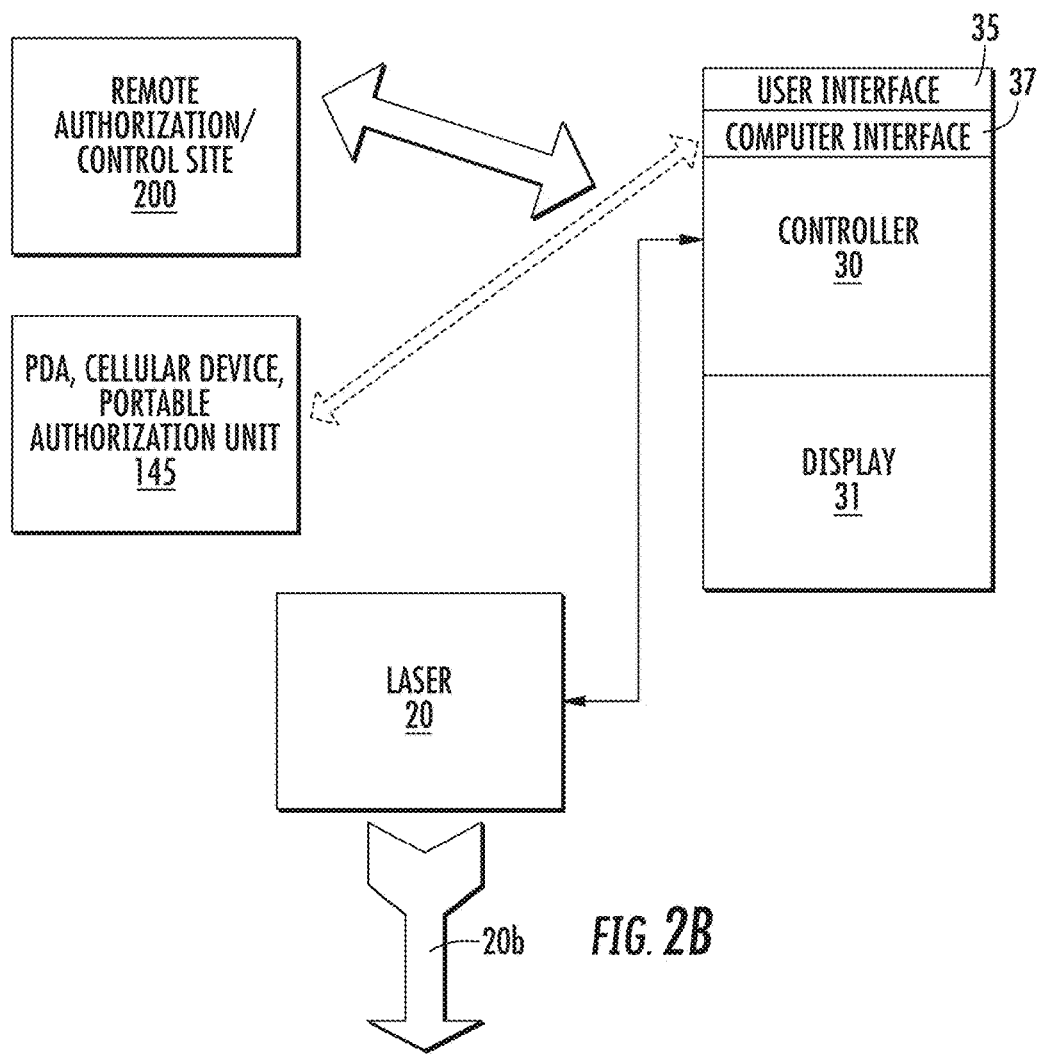
FIG. 2B is a schematic illustration of an excimer laser system similar to that shown in FIG. 2A, but illustrating that the system may include a remote control/authorization site according to embodiments of the present invention.

FIG. 2B illustrates that the system 10 can include a remote control/authorization site 200 that can electronically communicate with the local system site. The remote site 200 can communicate with the local site, the local system 10 and/or the portable device 145 using a global computer network (e.g., the Internet). The remote system 200 can directly activate the local system 10 or can transmit the authorization code to the controller 30 and/or UI 35 or another communications device 145 that receives the electronic authorization code 45e. The controller 30 can include a computer interface 37 that allows the internet connection or the wireless connection to the device 145.

The device 145 can wirelessly communicate with a workstation (UI 35, controller 30, display 31). The device 145 and/or system 10 can communicate with a computer at the remote site 200, and can include a portal and/or presby-Application.

The system 10 can be configured to automatically select the presbyopia treatment ablation profile (and associated laser ablation control parameters) upon input of a presby-specific authorization code that can be provided by the card 45 (FIG. 2A) or electronically 45e to the controller 30, UI 35, or to another communications device 145. The electronic authorization code can be presby-specific or may be a general activation code for the excimer laser.

The electronic authorization can be provided in reply to a request and payment using a WEB (e.g., Internet) portal that allows such a request.

The remote site 200 can include a service to maintain a deposit account that authorizes payment from this account for each requested authorization or a number of requests can be pre-paid by the local site. The authorization codes that are paid for can be sent in a bundle with each being unique or can be transmitted in a format that allows for a limited number of re-uses. Alternatively, the authorization codes can be generated only when a user requests them or temporally synched to a planned use date. The WEB portal can also allow the user to identify the excimer laser system being used, the time and date of the procedure and the like. The system 10 can communicate with the remote site (e.g., remote computer and/or server) 200 via the internet (or even an intranet) with the appropriate use of firewalls for patient privacy and compliance with HIPPA (Health Insurance Portability and Accountability Act) or other regulatory rule or authority.

In some embodiments, the remote site 200 can monitor the number of activations at the local sites and electronically alert them before their pre-paid activations are depleted. The monitoring can be via the Internet using local detectors (sensors) that detect each laser activation and/or power down. This data as well as the type of procedure selected for each procedure can be correlated and sent to or monitored by the remote site 200.

In some embodiments, the remote site 200 can deactivate the local systems (or prevent activation of the excimer laser) if an operating parameter is deemed to need calibration or if certain parameters are deemed to need service. That is, the local systems 10 can include various sensors that detect for various defined operating conditions, drift temperature associated with certain components, laser power or drift and the like. The remote system 200 can disable the local system and send an alert or otherwise notify the local site if service or repair is deemed appropriate.

In some embodiments, the local excimer laser 20 is subject to deactivation by the remote site pursuant to defined contract rules such as breach of certain contractual provisions. For example, the remote site 200 can disable the local system 10 if the remote site 200 determines that the local system 10 is bypassing the use of authorization codes (or somehow uses the same code more than once), misuses the laser system 10, if the local site is in default on a scheduled payment, if the local site user is still operating with a double card for procedures identified as single card presby procedures, and the like.

In some embodiments, the local system 10 can include an RFID tag or GPS receiver that allows the remote system 200 to monitor the location of the system 10 to prevent unauthorized movement. The remote system 10 can deactivate or disable the laser 20 and/or controller 30 if unauthorized movement is detected.

The controller 30 can include a digital signal processor and/or an Application Specific Integrated Circuit (ASIC) (e.g., ASIC and/or processor with software) that includes or executes part or all of the instructions, e.g., computer readable program code for generating the presbyopia ablation profile. The controller 30 can include a data processing system which may, for example, be incorporated or integrated into the processor. The controller and/or processor (and reader, where used) can communicate with or include electronic memory. The processor can be any commercially available or custom microprocessor. The memory is representative of the overall hierarchy of memory devices containing the software and data used to implement the functionality of the data processing system. The memory can include, but is not limited to, the following types of devices: cache, ROM, PROM, EPROM, EEPROM, flash memory, SRAM, and DRAM.

Figure 3:
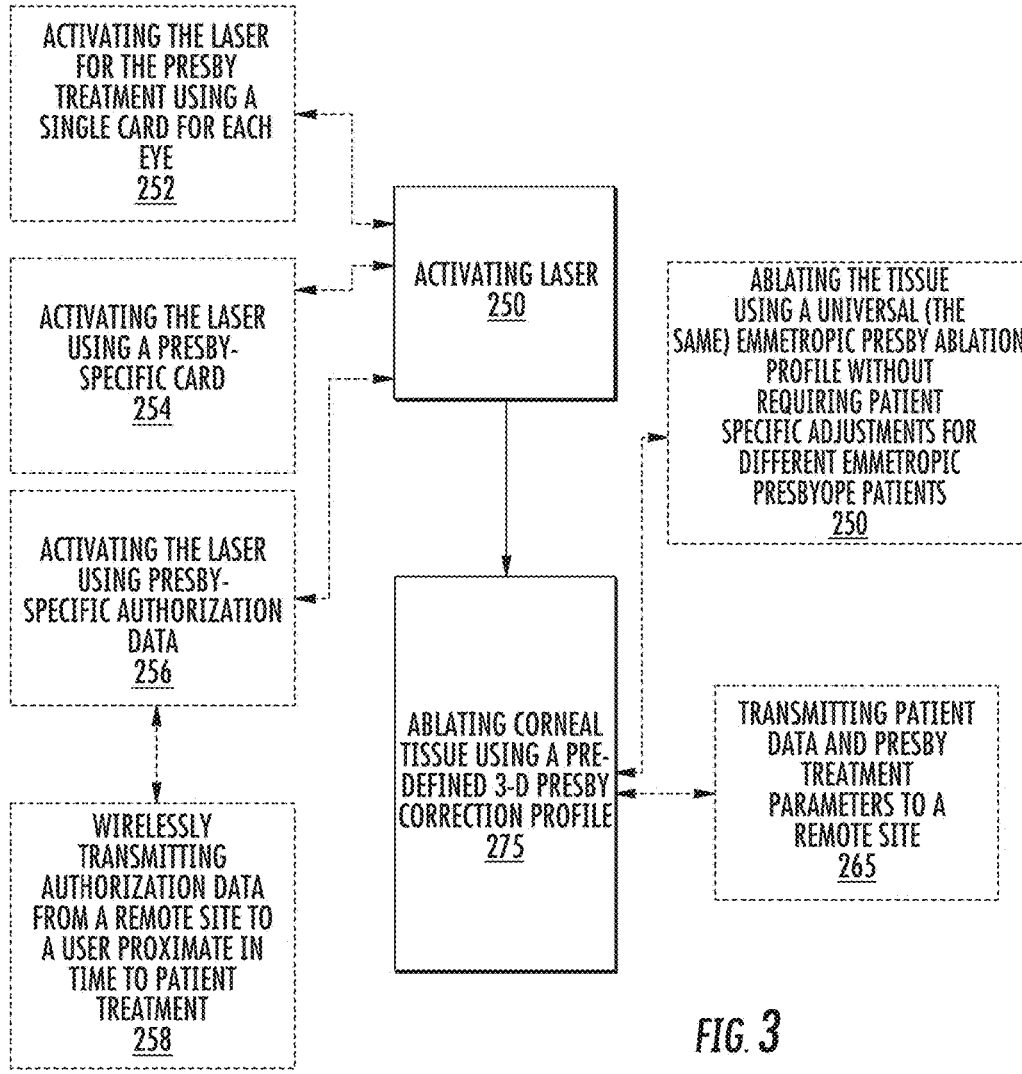
FIG. 3 is a flow chart of operations that can be used to treat presbyopia according to embodiments of the present invention.

FIG. 3 illustrates examples of steps that can be used to carry out embodiments of the present invention. As shown, an excimer laser is activated (block 250) and corneal tissue is ablated using a pre-defined 3-D ablation profile (which may include simultaneously ablating tissue with combined myopic and hyperopic correction profiles for some patients) (block 275).

FIG. 5A illustrates a three-dimensional ablation profile of "dish" and "donut" ablations using combined (concurrent, single card) ablation profiles shown in the adjacent graphs of FIGS. 5B and 5C to provide the desired PRESBY treatment.

The activating step can be based on a laser activation card whereby the excimer laser is activated only once for each eye to carry out the presbyopia ablation treatment (block 252). The activating step can be based on the use of a presby-specific laser activation card (block 254) which may have an increased cost associated with it relative to other single-use activations. The activating step can be based on presby-specific authorization data (code) entered by a user manually or wirelessly (block 256). If the latter, the authorization data can be transmitted from a remote site to a user site proximate in time to a patient treatment (block 258). This can allow more real-time control of the use of the excimer laser system to enforce contract provisions.

Optionally, the ablating step is carried out using a universal presby-ablation profile without requiring patient-specific in situ adjustments for emmetropic presbyope patients (e.g., the presby-ablation profile is the same for most if not all emmetropic presbyope patients) (block 260). Optionally, patient data and presby-treatment parameters (associated with the laser operation and/or delivered ablation profile) can be transmitted to a remote site (block 265).

Figure 4:
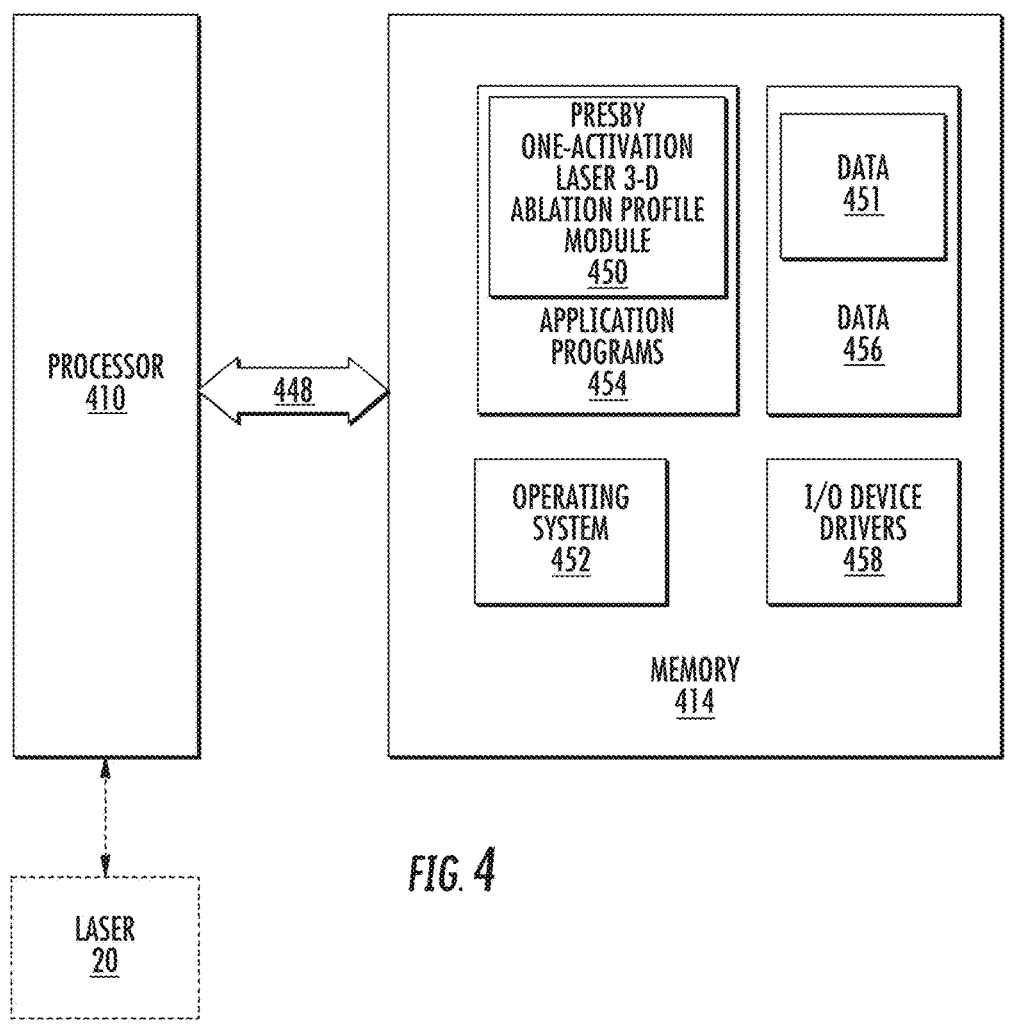
FIG. 4 is a block diagram of a data processing system according to embodiments of the present invention.

FIG. 4 is a block diagram of exemplary embodiments of data processing systems 400 that illustrates systems, methods, and computer program products in accordance with embodiments of the present invention. The processor 410 (which can optionally be part of the controller 30) communicates with the memory 414 via an address/data bus 448. The processor 410 can be any commercially available or custom microprocessor. The memory 414 is representative of the overall hierarchy of memory devices containing the software and data used to implement the functionality of the data processing system 405. The memory 414 can include, but is not limited to, the following types of devices: cache, ROM, PROM, EPROM, EEPROM, flash memory, SRAM, and DRAM.

As shown in FIG. 4, the memory 414 may include several categories of software and data used in the data processing system 405: the operating system 452; the application programs 454; the input/output (I/O) device drivers 458; the presby-one-activation ablation profile generator module 450; and the data 456. The data 456 may include a table of operational parameters, including power output and duration to generate the desired ablation profile 451. As will be appreciated by those of skill in the art, the operating system 452 may be any operating system suitable for use with a data processing system, such as OS/2, AIX, OS/390 or System390 from International Business Machines Corporation, Armonk, N.Y., Windows CE, Windows NT, Windows95, Windows98 or Windows2000, Windows VISTA from Microsoft Corporation, Redmond, Wash., Unix or Linux or FreeBSD, Palm OS from Palm, Inc., Mac OS from Apple Computer, LabView, or proprietary operating systems. The I/O device drivers 458 typically include software routines accessed through the operating system 452 by the application programs 454 to communicate with devices such as I/O data port(s), data storage 456 and certain memory 414 components and/or the dispensing system 420.

The application programs 454 are illustrative of the programs that implement the various features of the data processing system 405 and preferably include at least one application which supports operations according to embodiments of the present invention. Finally, the data 456 represents the static and dynamic data used by the application programs 454, the operating system 452, the I/O device drivers 458, and other software programs that may reside in the memory 414.

While the present invention is illustrated, for example, with reference to the signal generator module 450 being an application program in FIG. 4, as will be appreciated by those of skill in the art, other configurations may also be utilized while still benefiting from the teachings of the present invention. For example, the module 450 may also be incorporated into the operating system 452, the I/O device drivers 458 or other such logical division of the data processing system 405. Thus, the present invention should not be construed as limited to the configuration of FIG. 4, which is intended to encompass any configuration capable of carrying out the operations described herein.

The I/O data port can be used to transfer information between the data processing system 405 and the remote site 200 or another computer system or a network (e.g., an intranet and/or the Internet) or to other devices controlled by or in communication with the processor. These components may be conventional components such as those used in many conventional data processing systems which may be configured in accordance with the present invention to operate as described herein.

While the present invention is illustrated, for example, with reference to particular divisions of programs, functions and memories, the present invention should not be construed as limited to such logical divisions. Thus, the present invention should not be construed as limited to the configuration of FIG. 4 but is intended to encompass any configuration capable of carrying out the operations described herein.

The flowcharts, schematic illustrations and block diagrams of certain of the figures herein illustrate the architecture, functionality, and operation of possible implementations of excimer laser systems according to the present invention. In this regard, each block in the flow charts, schematic illustrations or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order, depending upon the functionality involved.

The one-card presbyopia treatment may be performed several times on a patient as the patient ages. This is due to the fact that the treatment is directed to treat for the action of the ciliary muscle for which the accommodation capacity to focus from distance to a near object decreases up until about age 70.

In some embodiments, the treatment systems can be used for patients with various incoming refraction requirements. FIGS. 6A-6C through FIGS. 12A-12C show examples of representative ablation patterns for patients with myopia (−5, −3, and −1 diopters), emmetropia, and hyperopia (+1, +3, and +5 diopters). Although not shown, other diopter increments may be used including, +−2 and +/−4.

An exemplary two-dimensional equation of a cross-section of an ablation profile is defined by Equation 1.

$$Y=(1.84-10.4*m)*\text{EXP}(-\text{EXP}((x-2.1)/0.572))+(-0.78+38.8*h)*(\text{EXP}((x-3.16)/0.665)*\text{EXP}(-\text{EXP}((x-3.16)/0.665))-0.004) \quad \text{Equation 1}$$

where:
 Y=ablation depth (μm)
 X=distance from center of cornea (mm)
 M=myopic ablation
 H=hyperopic ablation This formula yields a two-dimensional curve that describes a hemi cross-section of the ablation. The output is ablation depth versus distance from the center of the cornea. This can be converted to a three dimensional representation by revolving the curve around a line at the center of the cornea.

Figure 6B:
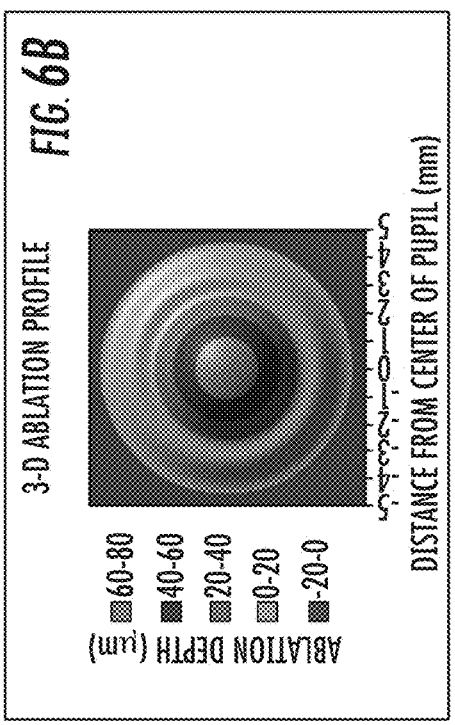
FIGS. 6A-6C through FIGS. 12A-12C show examples of representative ablation patterns or profiles for treating certain patients with various conditions, including myopia (−5, −3, and −1 diopters), emmetropia, and hyperopia (+1, +3, and +5 diopters).
Figure 6C:
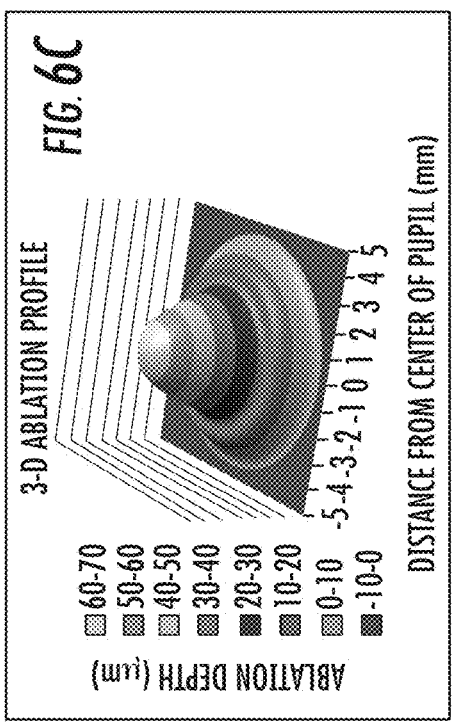
Figure 6A:
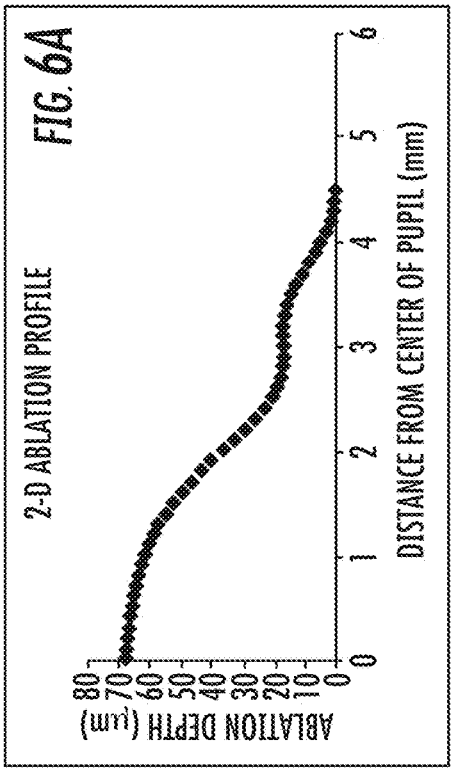
Figure 9A:
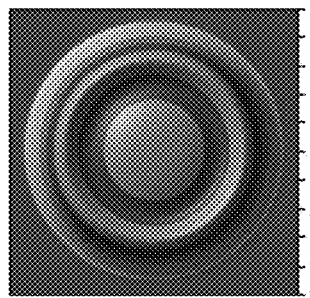
Figure 9B:
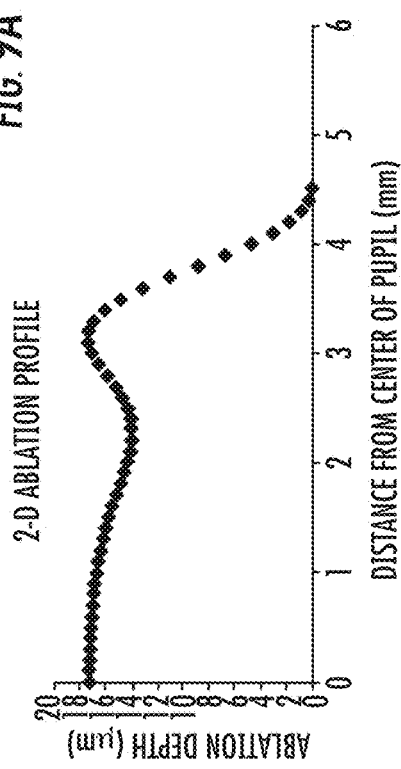
Figure 9C:
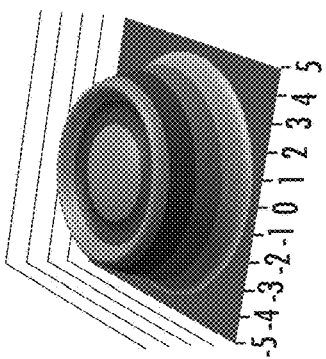
Figure 10B:
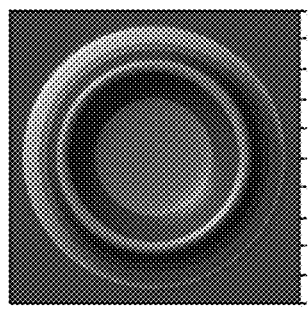
Figure 10C:
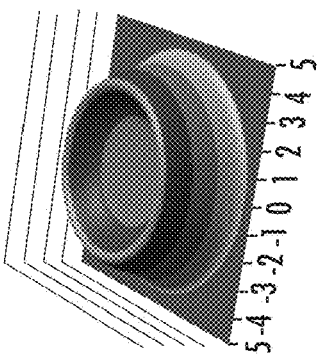
Figure 10A:
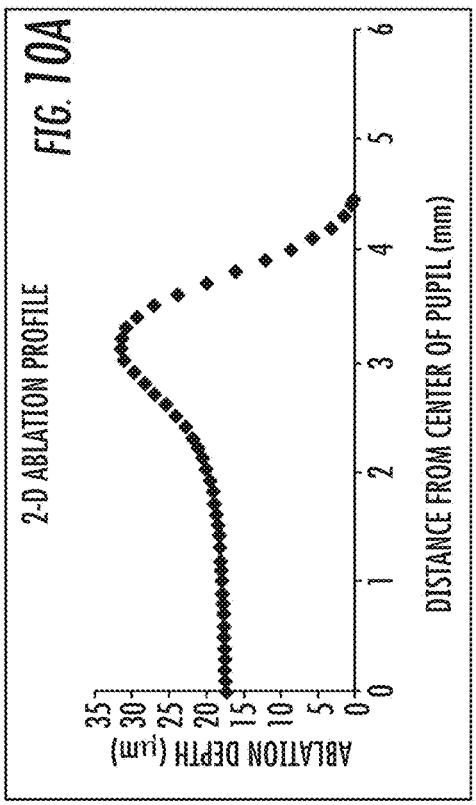
Figure 12B:
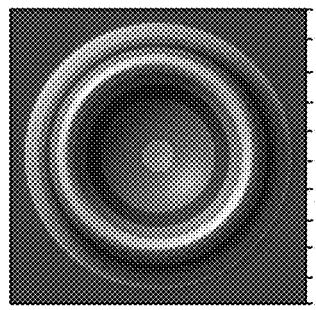
Figure 12C:
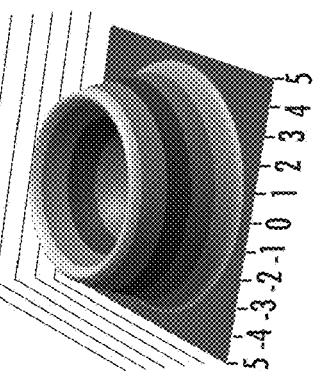
Figure 12A:
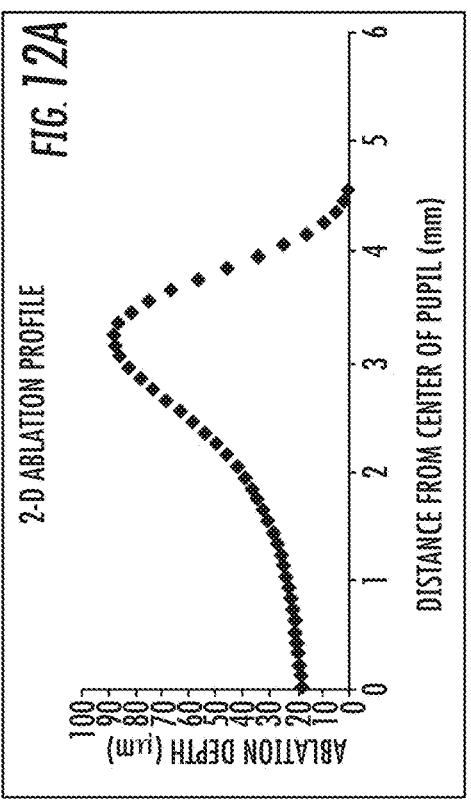

FIGS. 6A, 7A, 8A, 9A, 10A, 11A and 12A illustrate respective examples of 2-D ablation profiles, ablation depth (μm) versus distance from the center of the cornea or pupil (mm). This profile can be converted to a three dimensional representation shown in the associated corresponding figures (e.g., FIGS. 6B and 6C for FIG. 6A) by revolving the 2-D curve around a line at the center of the cornea. FIGS. 6B, 7B, 8B and the like are front or top views and FIGS. 6C, 7C, 8C and the like are corresponding side perspective views. Note that the scales used in FIGS. 7B and 7C are different as are the scales used in FIGS. 12B and 12C. That is, FIGS. 7B and 12B have a greater graduated (fine) scale (6 ranges) relative to the four and three ranges, in FIG. 7B and FIG. 12C, respectively.

In some embodiments, if the patient requires refraction for optimized distance vision (r) is less than 0, then the myopic ablation (M) equals r−1.5 (diopters) in about a 5.5 mm optical zone and the hyperopic ablation (H) is +1.25 diopters in about a 6.0 mm optical zone.

In some embodiments, the system 10 can configure the UI 35 to include a presby-ablation operative mode with an associated data entry screen or screens for entering the desired presby-ablation input parameters used to generate the corresponding ablation profile: e.g., an Rx value for myopic vision correction and an Rx value for hyperopic vision correction. These Rx input parameter values can be selected from a defined range of values for each Rx option or voice recognition can be used to accept the input (or manual key entry can be used as well). Similarly, where an optical zone input parameter(s) is used, this input parameter can be selected based on a defined set of values, a pull down list, or manually (voice recognition, hard key entry) entered. Once the patient input parameters are defined/selected, the ablation profile can be generated using a defined presby-ablation equation that generates the 3-D ablation profile.

In some embodiments, if the patient requires refraction for optimized distance vision (r) is greater than 0, then the myopic ablation (M) equals −1.5 (diopters) in about a 5.5 mm optical zone and the hyperopic ablation(H) is r+1.25 (diopters) in about a 6.0 mm optical zone.

In some embodiments, if the patient has emmetropia, then the myopic ablation (M) equals −1.5 diopters in about a 5.5 mm optical zone and the hyperopic ablation (H) is +1.25 diopters in about a 6.0 mm optical zone.

Non-Limiting Examples will be discussed below.

EXAMPLES

A patient presents for treatment to improve reading range (near object) using LASIK or PRK vision correction. The patient is typically between about 40-45 or older although the treatment may be particularly beneficial for those between 40-55 years of age or even older (this can be patient-specific, but it is contemplated that the treatment can be successful for patients even over 65).

The laser is activated a single time to generate a defined presbyopia 3-D ablation profile for a respective eye. The laser is powered down and then reactivated to treat the next eye. The patient typically has a +2.0 or less correction for reading (but may be up to about +3.0, or even more). In some embodiments, the patients suitable for this procedure have a Rx reading correction range of between about −1.25 to about −7.5 (myopic correction) and between about 1.25 and about 3.75 (hyperopic correction). The optical zone parameter(s), where used, can include a single parameter or two or more discrete parameters. These optical zone parameters can be adjustable, constant and/or weighted or scaled. The optical zone parameters can include a myopic optical zone parameter (mm) and a hyperopic optical zone parameter (mm), between about 5 to about 6.5 and between about 6 to about 7, respectively.

Further, examples of equations that can be used to define suitable 3-D ablation profiles are provided below.

Exemplary Ablation Profiles Based on Gumbel Distributions $$D = 17.5 * e^{-e\left(\frac{x-2}{0.65}\right)} + \frac{35}{0.75} * e^{\left(\frac{x-3.25}{0.75}\right)} * e^{-e\left(\frac{x-3.25}{0.75}\right)} \qquad \text{EQN 2}$$

Figure 13:
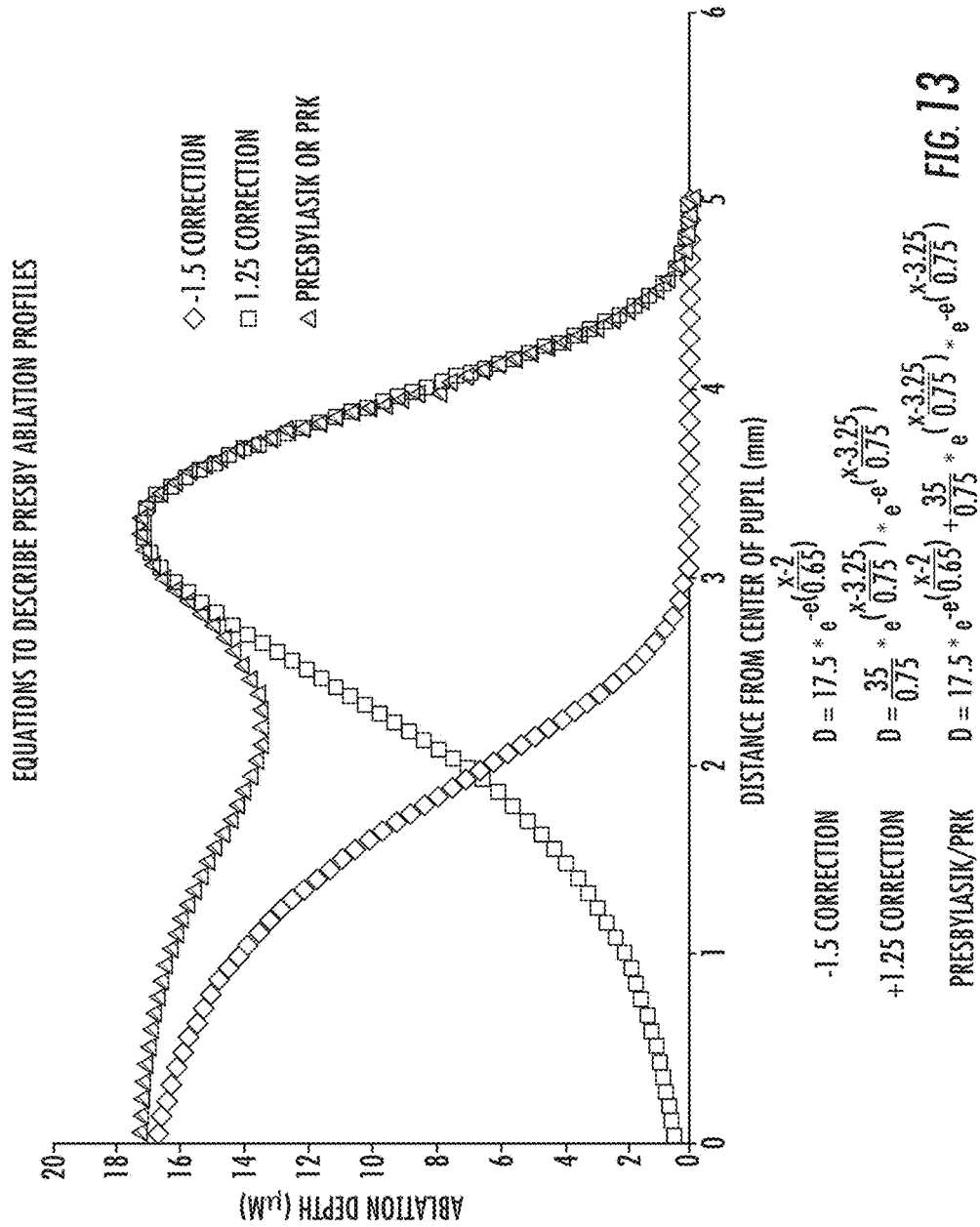
FIG. 13 is a graph of ablation depth versus distance from the center of a pupil (mm) for separate corrections and a combined ablation correction (e.g., the presbyLASIK/PRK curve).

Equation 2 was generated using a Gumbel distribution for a particular correction, e.g., −1.5 correction with a +1.25 correction. FIG. 13 illustrates an ablation profile using this equation (the "Presby" line) shown relative to two separate corrections for ablation depth versus distance from the center of the pupil. This equation can be further optimized for various presby ablation profiles or modified to appear in a different format (3D, etc).

Equation 3 is an exemplary equation for the Presby-ablation profile based on a modified Gumbel distribution. A probability distribution function can be used to create a myopic ablation profile, and a cumulative distribution function can be used to create a hyperopic ablation profile. Combining the profiles results in a Presby-profile. The equation for this profile is defined in Equation 3.

Equation 3

$$D=(1.84-10.4*Rx\_m)*\exp(-\exp((x-2.10)/0.572))+(-0.780+38.8*Rx\_h)*(\exp((x-3.16)/0.665)*\exp(-\exp((x-3.16)/0.665))-0.004) \qquad [3]$$

where:
D: ablation depth (μm)
x: is distance from center (mm)
Rx_m: myopic correction (D)
Rx_h: hyperopic correction (D)

Because it is possible for the second part (hyperopic) of Equation [3] to become negative, this part of the profile is assumed to have a minimum value of zero. This will also be true for other Gumbel equations, e.g., Equations 4 and 4' below.

Equation [3] assumes optical zones of 5.5 mm and 6 mm for the myopic and hyperopic corrections, respectively. In order to account for a variety of optical zones, the constants above can be scaled by zone-dependent parameters. The equation or formula used to generate the desired ablation profiles can be defined using at least one additional parameter for optical zone.

Equation 4 is an example of a modified version of Equation 3.

Equation 4

$$D=(1.84-10.4*Rx\_m)*(0.627*z\_m-2.41)*\exp(-\exp((x-2.10*(0.326*z\_m-0.802))/(0.572*(0.499*z\_m-1.69))))+(-0.780+38.8*Rx\_h)*(0.413*z\_h-1.48)*(\exp((x-3.16*(0.0914*z\_h+0.452))/(0.665*(0.0914*z\_h+0.452)))*\exp(-\exp((x-3.16*(0.0914*z\_h+0.452))/(0.665*(0.0914*z\_h+0.452))))-0.004) \qquad [4]$$

where:
D: ablation depth (μm)
x: is distance from center (mm)
Rx_m: myopic correction (D)
Rx_h: hyperopic correction (D)
z_m: myopic optical zone (mm)
z_h: hyperopic optical zone (mm)

Exemplary Profiles Based on Lognormal Distributions

The Presby profiles can be based on modified lognormal distributions. The probability distribution function can create a myopic ablation profile, and the cumulative distribution function can create a hyperopic ablation profile. Combining the profiles results in the Presby profile. An example of an equation for this profile is in Equation 5.

Equation 5:

$$D=(0.973-5.48*Rx\_m)*(1+erf((\ln(3.13-x)-0.250)/0.824))+(-0.602+28.5*Rx\_h)/(5.12-x)*\exp(-(((\ln((5.12-x)/20.0)+2.21)/0.511)^2)) \quad [5]$$

where:
D: ablation depth (μm)
x: is distance from center (mm)
Rx_m: myopic correction (D)
Rx_h: hyperopic correction (D)

Because the natural log in Equation [5] is undefined for negative numbers, the first part of the equation (myopic) is assumed to equal zero for x>3.13. Similarly, the entire profile is assumed to equal zero for x>5.12.

Equation [5] assumes optical zones of 5.5 mm and 6 mm for the myopic and hyperopic corrections, respectively. In order to account for a variety of optical zones, the constants above can be scaled by one or more optical zone variables, e.g., zone-dependent parameters. Doing so results in Equation 6.

Equation 6

$$D=(0.973-5.48*Rx\_m)*(0.550*z\_m-2.07)*(1+erf((\ln(3.13*(0.229*z\_m-0.271)-x)-0.250*(1.59*z\_m-8.05))/(0.824*(0.158*z\_m-0.048))))+(-0.602+28.5*Rx\_h)*(0.109*z\_h+0.348)/(5.12*(-0.010*z\_h+1.06)-x)*\exp(-(((\ln((5.12*(-0.010*z\_h+1.06)-x)/(20.0*(-0.006*z\_h+1.03)))+2.21*(0.081*z\_h+0.517))/(0.511*(0.124*z\_h+0.258)))^2)) \quad [6]$$

where:
D: ablation depth (μm)
x: is distance from center (mm)
Rx_m: myopic correction (D)
Rx_h: hyperopic correction (D)
z_m: myopic optical zone (mm)
z_h: hyperopic optical zone (mm)

Because the natural log in Equation [6] is undefined for negative numbers, the first part of the equation (myopic) is assumed to equal zero for x>3.13*(0.218*z_m−0.212). Similarly, the entire profile is assumed to equal zero for x>5.12*(−0.010*z_h+1.06).

Figure 14B:
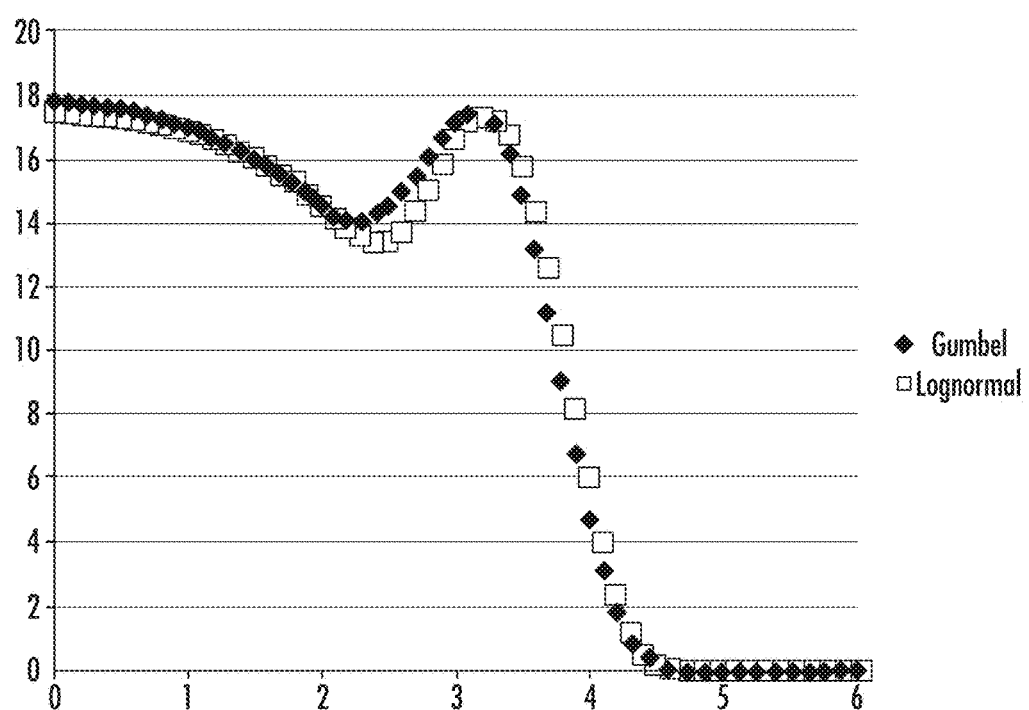
FIG. 14B is a graph of lognormal versus Gumbel-based ablation profiles (μm for ablation depth versus mm for distance from center) based on the data from the spreadsheet in FIG. 14A according to some embodiments of the present invention.

FIG. 14A is a spreadsheet table of adjustable input parameters. FIG. 14B shows plots of log versus Gumbel-based equations with adjustable input parameters. The spreadsheet data includes duplicate columns in order to make use of if( ) statements in Excel. Specifically, for the Gumbel distribution, the first D_h column has negative values which are assumed to be zero in the second column. For the lognormal data, the first columns for both D_m and D_h have some values that are undefined (when the argument for ln( ) is negative), and so the second columns assume those values to be zero. This is one exemplary way of implementing the clauses at the end of each equation in the document, as a simple way to create if( ) statements within the equations themselves. This allows a user to modify the parameters using this equation format. Other analysis or data manipulation types may be used.

The above-examples of Presby-ablation profile equations employ two optical zone parameters "z_m and z_h" (for the myopic and hyperopic profiles). However, the equations can be simplified to use only a single optical zone parameter as described in Equations 4' and 6' below (modified versions of Equations 4 and 6, respectively).

$$D=(1.84-10.4*Rx\_m)*(0.627*z-2.41)*\exp(-\exp((x-2.10*(0.326*z-0.802))/(0.572*(0.499*z-1.69))))+(-0.780+38.8*Rx\_h)*(0.413*z-1.48)*(\exp((x-3.16*(0.0914*z+0.452))/(0.665*(0.0914*z+0.452))))*\exp(-\exp((x-3.16*(0.0914*z+0.452))/(0.665*(0.0914*z+0.452))))-0.004) \quad [4']$$

where:
D: ablation depth (μm)
x: is distance from center (mm)
Rx_m: myopic correction (D)
Rx_h: hyperopic correction (D)
z: optical zone (mm)

$$D=(0.973-5.48*Rx\_m)*(0.550*z-2.07)*(1+erf((\ln(3.13*(0.229*z-0.271)-x)-0.250*(1.59*z-8.05))/(0.824*(0.158*z-0.048))))+(-0.602+28.5*Rx\_h)*(0.109*z+0.348)/(5.12*(-0.010*z+1.06)-x)*\exp(-(((\ln((5.12*(-0.010*z+1.06)-x)/(20.0*(-0.006*z+1.03)))+2.21*(0.081*z+0.517))/(0.511*(0.124*z+0.258)))^2)) \quad [6']$$

where:
D: ablation depth (μm)
x: is distance from center (mm)
Rx_m: myopic correction (D)
Rx_h: hyperopic correction (D)
z: optical zone (mm)

Because the natural log in Equation [6'] is undefined for negative numbers, the first part of the equation (myopic) is assumed to equal zero for x>3.13*(0.218*z−0.212). Similarly, the entire profile is assumed to equal zero for x>5.12*(−0.010*z+1.06).

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, if used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method of treating presbyopia, comprising:
activating an excimer laser of a surgical excimer laser system only a single time to transmit a defined three-dimensional multi-focal ablation profile; and ablating a cornea of an eye of a respective patient to treat presbyopia and provide near and distance vision acuity in the eye in response to the transmitted defined three-dimensional multi-focal ablation profile by the single activation of the excimer laser, wherein the defined three dimensional multi-focal ablation profile combines myopic and hyperopic corrections into a single composite ablation profile of ablation depth versus distance from a center of at least one of a pupil or the cornea.

2. The method of claim 1, wherein the three-dimensional multi-focal ablation profile transmitted by the single activation of the excimer laser generates a plurality of dish and donut shaped ablation profiles such that ablation depth can increase or decrease with distance from the center of at least one of the pupil or cornea.

3. The method of claim 1, wherein the transmitted three-dimensional multi-focal ablation profile is a presby ablation profile and creates a prolate shaped cornea with negative asphericity resulting in a multi-focal cornea and/or increasing depth of field without reducing distance acuity.

4. The method of claim 1, wherein the surgical excimer laser system comprises a user interface in communication with a controller that allows a user to enter an authorization code that allows and/or directs the surgical excimer laser system to activate to carry out the activating the single time, and wherein the method further comprises electronically selecting a set of ablation depths and distances from the center of the cornea for the defined three dimensional multi-focal ablation profile based on patient-specific input parameters including an input for myopic vision correction and an input for hyperopic vision correction.

5. The method of claim 1, wherein the surgical excimer laser system has or is in communication with a computer interface that allows a remote site to control activation of the surgical excimer laser system via the Internet, and wherein the computer interface controls a cumulative number of single multi-focal specific activations of the surgical excimer laser system for different patients and/or different eyes of a respective patient based on a number of laser-specific and/or site-specific pre-paid activations.

6. The method of claim 1, wherein the activating step is carried out using at least one controller that is in communication with the surgical excimer laser system, the at least one controller configured to direct the surgical excimer laser system to generate the defined three dimensional multi-focal ablation profile for a respective eye of a patient using a respective single activation of the excimer laser of the surgical excimer laser system.

7. The method of claim 6, wherein the method further comprises calculating the defined three dimensional multi-focal ablation profile using a patient-specific parameter for myopic correction having a set of ablation depths versus distances from the center of at least one of the pupil or cornea and a patient-specific parameter for hyperopic correction having a set of ablation depths versus distances from the center of at least one of the pupil or cornea.

8. The method of claim 6, wherein the at least one controller comprises a mathematical equation that includes first and second optical zone parameters adjustable for respective patients and/or an eye of a respective patient, one for a myopic optical zone and one for a hyperopic optical zone to provide the defined three dimensional multi-focal ablation profile.

* * * * *